United States Patent [19]

Black et al.

[11] Patent Number: 4,931,469

[45] Date of Patent: Jun. 5, 1990

[54] NOVEL PESTICIDES, PREPARATION AND USE

[75] Inventors: Malcolm H. Black; Robert J. Blade, both of Tring, England

[73] Assignee: Burroughs Wellcome Co., Research Triangle Park, N.C.

[21] Appl. No.: 205,572

[22] Filed: Jun. 8, 1988

Related U.S. Application Data

[60] Continuation of Ser. No. 881,125, Jul. 2, 1986, abandoned, which is a division of Ser. No. 540,801, Oct. 11, 1983, Pat. No. 4,855,086.

[30] Foreign Application Priority Data

Oct. 15, 1982 [GB] United Kingdom ................. 8229550
Dec. 21, 1982 [GB] United Kingdom ................. 8236346
Jun. 7, 1983 [GB] United Kingdom ................. 8313566

[51] Int. Cl.$^5$ ..................... A01N 37/10; A01N 37/12; A01N 37/18

[52] U.S. Cl. .................................... 514/617; 514/533; 514/538; 514/618; 514/621; 514/622

[58] Field of Search ............... 514/617, 618, 699, 622, 514/621, 533, 538

[56] References Cited

FOREIGN PATENT DOCUMENTS

| 8200110 | 5/1982 | European Pat. Off. ............ 514/617 |
| 46-25033 | 7/1971 | Japan .................................. 514/617 |
| 57-106651 | 7/1982 | Japan .................................. 514/617 |
| 681044 | 8/1979 | U.S.S.R. ............................. 514/617 |

Primary Examiner—Allen J. Robinson
Attorney, Agent, or Firm—Donald Brown

[57] ABSTRACT

The specification describes and claims methods of controlling acarine pests by application of a compound of Formula (I), methods of controlling arthropod pests by application of a compound of Formula (IA), compounds of Formula (IA) per se, pesticidal compositions comprising a compound of Formula (IA), and processes for preparing a compound of Formula (IA).

3 Claims, No Drawings

PESTICIDES, PREPARATION AND USE

This application is a continuation of application Ser. No. 881,125, filed 7/2/86, now abandoned, which is a division of application Ser. No. 540,801, filed 10/11/83, now U.S. Pat. No. 4,855,086.

This invention relates to novel compounds having activity against arthropods, processes for their preparation, formulations containing them and their use in controlling arthropod pests.

Certain amides of straight-chain w-(3,4-methylenedioxyphenyl)-alkenoic acids are constituents of oil extracted from the seeds of plants of the genus Piper, and some of these are known to possess insecticidal activity (Agric. Biol. Chem., 43(7) 1609–1611, 1979). A number of other compounds having a 3,4-methylenedioxyphenyl substituent have found use in the control of insects.

We have now discovered that certain novel w-aryl-alkenoic and -alkynoic acid amides also possess activity against insects and other arthropods, although they are without the 3,4-methylenedioxy substituent of the compounds described above. These novel compounds may be prepared by synthetic methods.

Accordingly, this invention provides a method of controlling pests of the Order Acarina by application to the pest or its environment a composition comprising a pesticidally effective amount of a compound of formula (I) in combination with one or more carriers, synergists or the like:

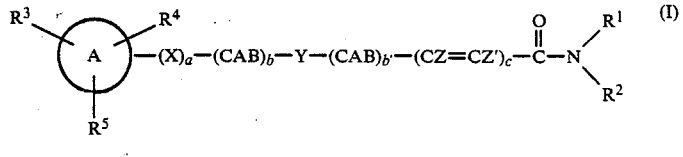

wherein:
$R^1$ and $R^2$ are the same or different and each is hydrogen, alkyl, $C_{3-8}$ cycloalkyl, ($C_{3-8}$ cycloalkyl)-alkyl, aryl, aralkyl or alkenyl, or $R^1$ and $R^2$ are linked to form a ring having 5, 6 or 7 ring atoms, any of which groups may be substituted;

(A) is an aromatic five- or six-membered carbocyclic or heterocyclic ring;

$R^3$, $R^4$ and $R^5$ are each independently hydrogen, halo, alkyl, alkenyl, alkoxy (except methylenedioxy), aryl, aralkyl, or $SO_2NR_2$ where R is alkyl, any of which groups may be substituted;

a is 0, 1 or 2;

each X is independently selected from C≡C and CZ=CZ';

each Z and Z' is independently selected from hydrogen, halo and alkyl;

Y is CAB, $CH_2OCH_2$ or $CH_2S(O)_fCH_2$ where f is 0, 1 or 2;

each A and B is independently selected from hydrogen, alkyl and halo provided that neither A nor B is halo in a group CAB which is α to an unsaturated carbon atom;

b and b', which may be the same or different, are 0 or an integer from 1 to 5, b and b' together totalling not more than 7;

and c is 0, 1 or 2 provided that a and c are not both 0

The configuration of any olefinic group conjugated to the CO group in Formula (I) is E.

The configuration of any olefinic group conjugated to the aromatic ring in Formula (I) may be either E or Z.

When used herein, "alkyl", "alkenyl" and "alkoxy" mean such groups having from 1 to 6 carbon atoms, such as methyl, ethyl, propyl, butyl, propenyl, methoxy and the like; "aryl" means an aromatic heterocyclic or carbocyclic group, such as phenyl, naphthyl, furyl or thienyl; "aralkyl" means an alkyl group substituted by an aryl group, such as benzyl; and "halo" means fluoro, chloro, bromo or iodo.

Suitable substituents, where present, in the groups $R^1$, $R^2$, $R^3$, $R^4$ and $R^5$ include alkoxy, alkyl, halo, hydroxy, oxo and the like.

When $R^1$ or $R^2$ is alkenyl, it is saturated in the α-position.

When $R^1$ and $R^2$ are linked, $NR^1R^2$ may represent pyrrolidino, piperidino, tetrahydropyridino and the like. A particularly preferred group of compounds of the invention are those of Formula (IA), which compounds per se also form a second aspect of the invention:

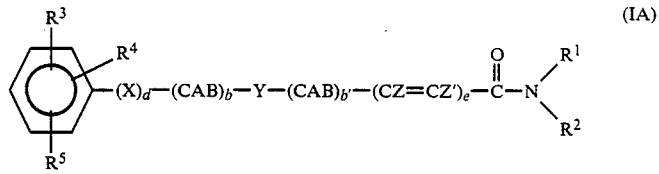

Wherein: $R^1$ to $R^5$, X, A, B, Y, Z and Z' are all as defined in Formula (I); d is 1 or 2; and e is 1 or 2:

Preferred compounds of Formula (IA) include those having one or more of the following features:

$R^1$ is hydrogen;

$R^2$ is alkyl, such as isobutyl;

$R^3$, $R^4$ and $R^5$ are independently hydrogen, halo such as chloro, alkyl such as methyl or tertiary butyl, substituted alkyl such as trifluoromethyl, or alkoxy such as methoxy;

X is C≡C, E—CH=CH or Z—CH=CH;

A and B are hydrogen;

Y is $CH_2$;

and b and b' are independently 0, 1 or 2.

The compounds of Formula (IA) may be prepared by methods analogous to those used for the preparation of compounds having the same functional groups. These methods include:

(a) the reaction of an acid of formula (II):

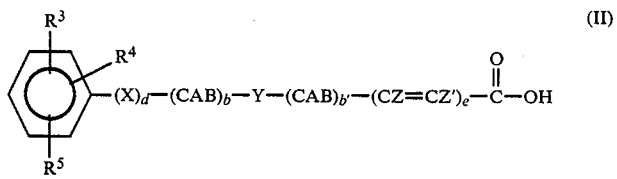

or a reactive derivative thereof such as an acid halide (e.g. the acid chloride) or acid phenyl N-phenylphosphoramide with an amine of formula $HNR^1R^2$;

(b) the reaction of a compound of formula (III):

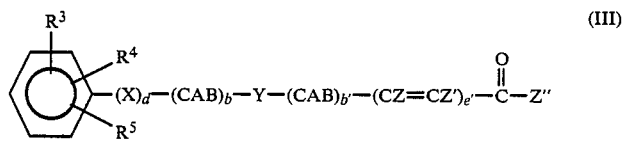

Where $Z''$ is H or alkyl
with a compound of formula (IV):

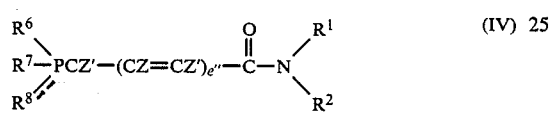

wherein each of $R^6$ and $R^7$ is alkyl, alkoxy or aryl; either $R^8$ is alkyl, alkoxy or aryl and the broken line does not represent a bond or $R^8$ is O and the broken line represents a bond; and $E'$ is 0 and $E''$ is 0 or 1, or $E'$ is 1 and $E''$ is 0;

(c) for the preparation of those compounds wherein Y is $CH_2OCH_2$ or $CH_2SCH_2$, the reaction of a compound (V) with a compound (VI):

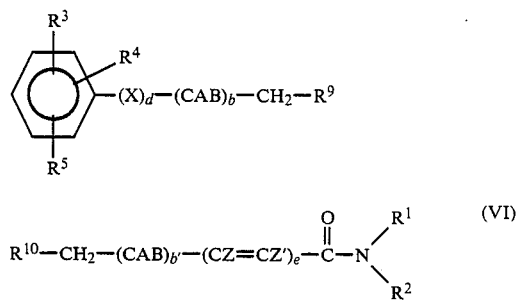

wherein $R^9$ and $R^{10}$ are groups which react together to produce an ether or thioether linkage, respectively;

(d) for the preparation of those compounds wherein at least one X is $CZ=CZ'$, the reaction of a compound of formula (VII) with a compound of formula (VIII):

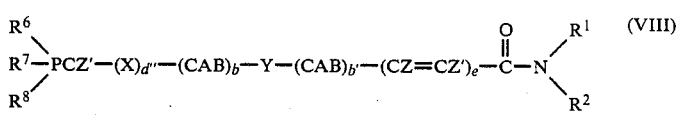

wherein $R^6$, $R^7$ and $R^8$ are defined in formula (IV), $Z''$ is hydrogen or alkyl and $d'$ is 0 and $d''$ is 0 or 1, or $d'$ is 1 and $d''$ is 0;

(e) the reaction of a compound (IX) with a compound (X):

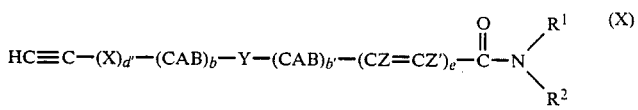

in the presence of copper and pyridine
where Hal is a halogen and d' is 0 or 1;

(f) for those compounds where neither R¹ nor R² is hydrogen, the reaction of a compound (XI) with a compound (XII):

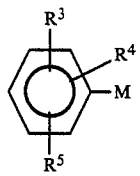
(XI)

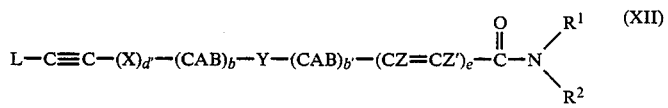
(XII)

where M is a metal, such as lithium or copper, L is halo or alkoxy and d' is 0 or 1;

(g) for those compounds where neither R¹ nor R² is hydrogen, the reaction of a compound (XIII) with a compound (XIV):

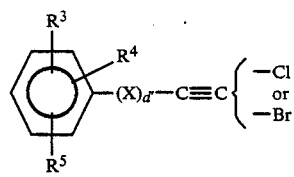
(XIII)

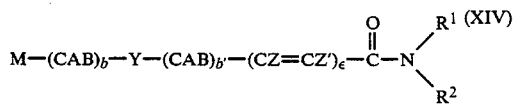
(XIV)

where d' is 0 or 1 and M is a metal, such as lithium, provided that neither A nor B attached to the terminal carbon atom is halo;
and thereafter optionally converting a first compound of formula (I) to a second compound of formula (I), for example (i) by hydrogenating a C≡C group to a C=C group where either or both of the X groups in the second formula (I) compound are C≡C; (ii) by hydrogenating a C≡C group or a C=C group or a C—C group; or (iii) by oxidising a Y group which is CH₂S(O)$_f$CH₂ to increase "f" by one.

Process (a) is normally carried out in an aprotic solvent, such as ether or benzene, optionally in the presence of a tertiary amine, such as triethylamine, but in the absence of water.

Processes (b) and (d) are carried out in a dry solvent, optionally in the presence of a base, and preferably in the absence of oxygen, e.g. under a nitrogen atmosphere. The hydrogenation of a C≡C group is normally carried out in a dry protic solvent such as methanol, in the presence of a palladium catalyst, such as Pd/C or Pd/BaSO₄. Preferably a catalyst poison is present to prevent further hydrogenation of the olefinic functions.

Process (c) may comprise the reaction of two alcohols in the presence of a dehydrating agent; or R⁹ and R¹⁰ may be OH or SH and halo, a base preferably being present; or other standard methods for the formation of ethers and thioethers, such as those described in "Compendium of Organic Synthetic Methods", Harrison and Harrison, Wiley Interscience, (New York) 1971.

Process (e) will preferably use standard oxidising agents used in the oxidation of sulphides to sulphoxides and sulphones, such as per-acids, e.g. perbenzoic acid, manganese dioxide, chromium trioxide, and the like.

The intermediates of formulae (II) - (XIV) may be prepared by standard methods. For example, the compounds of formulae (IV) and (VIII) may be prepared by the reaction of an appropriate phosphine, phosphonate or phosphite with an w-halo amide. Compounds of Formula (III) may be prepared by hydrolysis of a ketal ring.

The carbonyl-containing compounds (III) and (VII) may be prepared by oxidation of the corresponding alcohol, for example using pyridinium chlorochromate. The acid function in formula (II) may be prepared by hydrolysis of an ester, the ester being prepared by a conventional Wittig reaction, using e.g. an aldehyde and ethoxycarbonylmethylene triphenylphosphorane. The alcohols from which compounds (III), (VII) and (V) are prepared may be synthesised by the reaction of an O-protected w-halo alcohol with a phenylacetylene, phenylbutadiyne or phenylbutenyne. Suitable protecting groups include the tetrahydropyranyl group, which may be removed after the reaction of the alcohol with dihydropyran in the presence of an acid catalyst.

Alternatively, the alcohol from which the compounds of formulae (III) and (VII) are prepared may be synthesised by reaction of a compound of formula (XV):

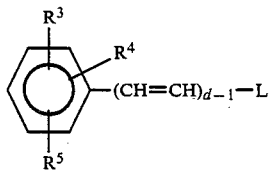
(XV)

where L is a leaving group (preferably iodo or bromo), with a compound of formula (XVI), the reaction being preferably catalysed by a palladium catalyst.

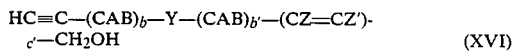
(XVI)

Process (b) or (d) will not be used when the desired final product would require the use of an intermediate where Z in the group CZO in (III) or (VII) is halo The compounds of formula (I) may be used to control arthropods such as insect and acarine pests.

The compounds of formula (I) may be used for such purposes by application of the compounds themselves or in diluted form in known fashion as a dip, spray, lacquer, foam, dust, powder, aqueous suspension, paste, gel, shampoo, grease, combustible solid, vapourising mat, wettable powder, granule, aerosol, emulsifiable concentrate, oil suspensions, oil solutions, pressure-pack, impregnated article or pour-on formulation. Dip concentrates are not applied per se, but diluted with water and the animals immersed in a dipping bath containing the dip wash. Sprays may be applied by hand or by means of a spray race or arch. The animal may be saturated with the spray by means of high volume application or superficially coated with the spray by means of light or ultra low volume application. Aqueous suspensions may be applied to the animal in the same manner as sprays or dips. Dusts may be distributed over the animals by means of a powder applicator or incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of formula (I) or acid addition salts thereof may be formulated either as formulations ready for use on the animals or as formulations requiring dilution prior to application, but both types of formulation comprise a compound of formula (I) in intimate admixture with one or more carriers or diluents. The carriers may be liquid, solid or gaseous or comprise mixtures of such substances, and the compound of formula (I) may be present in a concentration of from 0.025 to 99% w/v depending upon whether the formulation requires further dilution.

Dusts, powder and granules comprise the compound of formula (I) in intimate admixture with a powdered solid inert carrier for example suitable clays, kaolin, talc, mica, chalk, gypsum, vegetable carriers, starch and diatomaceous earths.

Sprays of a compound of formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of formula (I) in intimate admixture with a dispersing agent and one or more surface active agents.

Aqueous suspensions of a compound of formula (I) may comprise a suspension in water together with suspending, stabilizing or other agents. Aqueous solutions may also be formed from acid addition salts of a compound of the formula (I). The suspensions or solutions may be applied per se or in a diluted form in known fashion.

Greases (or ointments) may be prepared from vegetable oils, synthetic esters of fatty acids or wool fat together with an inert base such as soft paraffin. A compound of formula (I) is preferably distributed uniformly through the mixture in solution or suspension. Greases may also be made from emulsifiable concentrates by diluting then with an ointment base. Pastes and shampoos are also semi-solid preparations in which a compound of formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of formula (I) in a liquid medium which also contains a viscous oil to minimise spreading of the formulation on the surface of the animals. An avian or mammal host may also be protected against infestation of Acarine ectoparasites by means of carrying a suitably-moulded, shaped plastics article impregnated with a compound of formula (I). Such articles include impregnated collars, tags, bands, sheets and strips suitably attached to appropriate parts of the body.

The concentration of the compound of formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formulations such as pour-on formulations which in general will be deposited at a concentration in the range from 0.1 to 20.0% and preferably 0.1 to 10%.

Dusts, greases, pastes and aerosol formulations are usually applied in a random fashion as described above and concentrations of 0.001 to 20% w/v of a compound of formula (I) in the applied formulation may be used.

Insect pests include members of the orders Coleoptera (e.g. Anobium, Tribolium, Sitophilus, Anthonomus or Anthrenus spp.), Lepidoptera (e.g. Ephestia, Heliothis, Spodoptera or Tineola spp.), Diptera (e.g. Musca, Aedes, Culex, Glossina, Stomoxys, Haematobia, Tabanus, Hydrotaea, Lucilia, Chrysomia, Callitroga, Dermatobia, Hypoderma and Melophagus spp.), Phthiraptera (Malophaga e.g. Damalina spp. and Anoplura e.g. Linognathus and Haematopinus spp.), Hemiptera (e.g. Aphis or Cimex spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. Reticulitermes spp.), Siphonaptera (e.g. Ctenocephalides or Pulex spp.), Thysanura (e.g. Lepisma spp.), Dermaptera (e.g. Forficula spp.), and Pscoptera (e.g. Peripsocus spp.). Acarine pests include ticks, e.g. members of the genera Boophilus, Rhipicephalus, Amblyomma, Hyalomma, Ixodes, Haemaphysalis, Dermocentor and Anocentor, and mites and manges such as Tetranychus, Psoroptes, Psorergates, Chorioptes and Demodex spp.

The compounds exhibit killing and/or knockdown activity against arthropod pests, and can be used to control larval pests as well as adult pests.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example: one of the oxidase inhibitor class of synergists, such as piperonyl butoxide or NIA 16388; a second compound of the invention; or a pyrethroid pesticidal compound. When an oxidase inhibitor synergist is present in a formula of the invention, the ratio of synergist to compound of formula (I) will be in the range 25:1-1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

It will be understood that what we will claim may comprise:
(a) compounds of Formula (IA);
(b) processes for the preparation of compounds of Formula (IA);
(c) insecticidal and acaricidal compositions comprising a compound of Formula (IA) in admixture with a carrier.
(d) processes for the preparation of such pesticidal compositions; and
(e) methods for the control of acarine pests comprising the application to the pest or its environment of a compound of Formula (I)
(f) methods for the control of insect pests comprising the application to the pest or its environment of a compound of Formula (IA);
(g) synergised pesticidal compositions comprising a compound of Formula (I) or (IA); and
(h) potentiating or non-potentiating mixtures of a compound of Formula (I) or (IA) and another pesticidal compound.

The following examples are provided as illustrations of the invention, but should not be construed as limitations thereof.

In the examples, temperatures are in degrees Celsius, "ether" means diethyl ether, and "pb" means piperonyl butoxide.

EXAMPLE 1

N-Isobutyl-7-phenylhept-2E-en-6-ynamide (a) Phenylacetylene (4 g) was added to lithium amide in liquid ammonia (lithium 0.59 g/ammonia 250 ml) at −50°. Dry Me$_2$SO (70 ml) was added and the mixture was stirred for 1 hour. 1-Tetrahydropyranyloxy-3-bromopropane 8.7 g was added, followed by liquid ammonia (70 ml), and the mixture was stirred under reflux for 3 hours. Brine was added, and the ammonia was allowed to evaporate off. The reaction mixture was poured into ice, and the aqueous mixture extracted with ether. The ether extracts were washed with water, dried over MgSO$_4$ and purified by chromatography on silica, eluting with 3% ether in hexane followed by 1:1 hexane:ether. The solvent was evaporated from the eluate to yield 1-phenyl-5-tetrahydropyranyloxypent-1-yne (5 g) as a pale yellow liquid.

(b) A mixture of 1-phenyl-5-tetrahydropyranyloxypent-1-yne (0.2 g), absolute ethanol (4 ml) and p-toluenesulphonic acid (20 mg) was stirred at room temperature for 3 hours. The reaction mixture was diluted with water (40 ml) and extracted with ether (2×20 ml). The ether extracts were washed with saturated NaHCO$_3$ solution, dried over MgSO$_4$ and purified by chromatography on silica (20 g), eluting with 10% ether in hexane grading to 100% ether, followed by 10% ethyl acetate in ether. The solvent was removed to give 5-phenylpent-4-yn-1-ol as a colourless oil.

(c) A solution of 5-phenylpent-4-yn-1-ol (250 mg) in dry CH$_2$Cl$_2$ (2 ml) was added to a suspension of pyridinium chlorochromate (520 mg) in dry CH$_2$Cl$_2$ (3 ml). The mixture was stirred for 2.5 hours and diluted with ether, and the organic solution was decanted off. The oily residue was treated with ether (5×20 ml) and the extracts were washed successively with 5% NaHCO$_3$, water and brine. After drying, the solvent was removed to yield 5-phenylpent-4-ynal.

(d) 5-Phenylpent-4-ynal (3 g) in dry CH$_2$Cl$_2$ (30 ml) was added to a solution of carbethoxymethylenetriphenylphosphorane (10 g) in dry dichloromethane (20 ml), and the mixture was heated at reflux under a nitrogen atmosphere for 5 hours. The solvent was removed under reduced pressure, and the product was purified by chromatography on silica (150 g), eluting with 2:1 hexane:ether to yield ethyl 7-phenylhept-2E-en-6-ynoate (3.6 g).

(e) To a solution of ethyl 7-phenylhept-2E-en-6-ynoate (2.5 g) in methanol was added KOH (2.6 g) in water (6 ml). The mixture was stirred at 50° C. under a nitrogen atmosphere for 40 minutes, cooled, diluted with water (20 ml) and washed with ether (15 ml). The aqueous layer was acidified with 10% HCl and extracted with ether. The ether extracts were combined and dried over MgSO$_4$, and the solvent was distilled off (adding dry benzene (4 ml) to form azetrope with traces of water) to give 7-phenylhept-2E-en-6-ynoic acid (2 g) as a colourless oily solid.

(f) 7-Phenylhept-2E-en-6-ynoic acid (2 g) was dissolved in benzene (20 ml), thionyl chloride (2.5 ml) was added, and the mixture was refluxed under a nitrogen atmosphere for 45 minutes. Benzene and excess thionyl chloride were removed under reduced pressure and the residue was treated with benzene (2×4 ml), followed by evaporation, to leave a residue of 7-phenylhept-2E-en-6-ynoyl chloride. The acid chloride was dissolved in ether (20 ml), and triethylamine (1.5 ml) and isobutylamine (3 ml) were added. The mixture was stirred at room temperature for 2 hours then cooled to 0° C. The mixture was filtered and the filtrate was subjected to chromatography on silica (60 g), eluting with 100% hexane grading to 100% ether, to yield N-isobutyl-7-phenylhept-2E-en-6-ynamide mp 86°–8° C.

EXAMPLE 2

N-isobutyl-7-phenylhept-2E-en-6-ynamide (a) To a solution of the acid produced in Example 1 (e) (0.25 g) in ether (10 ml) was added oxalyl chloride (0.35 ml), and the mixture was allowed to stand at room temperature overnight. Dry benzene (4 ml) was added and the solution concentrated under reduced pressure. Excess oxalyl chloride was removed in a stream of nitrogen to give the acid chloride as an orange-yellow oil.

(b) A solution of isobutylamine (0.16 ml) and triethylamine (0.22 ml) in dry ether (5 ml) was added to a solution of the acid chloride in ether (3 ml). The mixture was stirred at −5° C. for 10 minutes then allowed to warm to room temperature. Isobutylamine (0.4 ml) was added and the mixture was stirred at room temperature for 1 hour. The mixture was diluted with ether and washed sequentially with water, dilute hydrochloric acid, dilute $NaHCO_3$ and water, and dried over $MgSO_4$. The solvent was removed to give N-isobutyl-7-phenyl-hept-2E-en-6-ynamide mp 86°–8° C.

EXAMPLE 3

N-isobutyl-7-phenylhepta-2E,6Z-dienamide

N-Isobutyl-7-phenylhept-2-en-6-ynamide (100 mg) and 5% $Pd/BaSO_4$ (17 ml) in dry methanol (3 ml) at 20° C. was treated with hydrogen until hydrogen uptake was 85% of theoretical. The mixture was diluted with methanol, filtered and the solvent was removed from the filtrate. The residue was treated with ether and the solvent removed in a stream of nitrogen. The product was purified by chromatography on silica (15 g), eluting with 1:1 ether:hexane grading to 100% ether to give N-isobutyl-7-phenylhepta-2E,6Z-dienamide (61 mg) as a yellow oil which crystallised on standing mp 42°–5° C.

EXAMPLE 4

N-isobutyl-9-phenylnona-2E,4E,8E/Z-trienamide (a) Methyl succinyl chloride was dissolved in xylene and a $Pd/BaSO_4$ catalyst and a catalyst poison were added. Hydrogen was passed through the mixture at 110° C. with vigorous stirring for 2 hours, when the theoretical quantity of HCl had been evolved. The mixture was cooled and filtered through Celite. Ethylene glycol and p-toluenesulphonic acid were added to the solution of methyl 3-formylpropionate and the mixture refluxed with a Dean and Stark trap to separate the water produced. The organic solution was subjected to fractional distillation, the fraction distilling at 96°–100° C./14 mmHg being collected to yield methyl 3,3-ethylenedioxypropionate (38 g).

(b) The ester produced in (a) above was added dropwise over 0.75 hours to a slurry of lithium aluminium hydride in ether, and cooled and water (20 ml) and saturated $NH_4Cl$ solution (200 ml) were added. The supernatant liquid was decanted off and extracted with ether. The extracts were dried over $MgSO_4$ and evaporated to give 3,3-ethylenedioxypropan-1-ol (15 g).

(c) The alcohol (5 g) was added to a slurry of pyridinium chlorochromate (12 g) in dry $CH_2Cl_2$ (100 ml) and the mixture was stirred overnight. Ether (100 ml) was added and the organic layer was decanted off. The residue was washed with ether (3×50 ml), and the ether extracts were combined and filtered through a Celite/charcoal (35:1) column. The solvent was removed in vacuo to yield 3,3-ethylenedioxypropanal (2 g).

(d) The aldehyde (3 g), and 3-carbethoxyprop-2E-enylene)-triphenylphosphorane (10 g) were refluxed in dry $CH_2Cl_2$ (50 ml) overnight. The solvent was evaporated and the residue was purified by chromatography on alumina, eluting with ether, to yield ethyl 8,8-ethylenedioxyocta-2E,4E/Z-dienoate (1.5 g) as a yellow oil.

(e) The product from (d) (1.5 g) was dissolved in tetrahydrofuran (10 ml), and water (5 ml) and concentrated HCl (5 drops) were added. The mixture was stirred at 50° C. for 1 hour, cooled and extracted with ether. The extract was washed with $NaHCO_3$ solution and water, and dried over $MgSO_4$. The solvent was removed to yield ethyl 8-oxo-octa-2E,4E/Z-dienoate (1.3 g) as a yellow oil.

(f) Sodium (1.5 g) was dissolved in dry ethanol (100 ml) and benzyltriphenylphosphonium chloride (8.5 g) in dry ethanol (40 ml) was added dropwise with stirring. The mixture was stirred for 0.5 hours, and the product of (e) above (4 g) in ethanol (10 ml) was added dropwise. The mixture was stirred for a further 0.75 hours, and the solvent was removed in vacuo. The residue was purified by chromatography on silica gel, eluting with 1:1 ether:hexane, to yield ethyl 9-phenylnona-2E,-4E8E/Z-trienoate (1.2 g) as a yellow oil.

(g) Using the process described in Example 1 (e) and (f), the ester was converted to N-isobutyl-9-phenyl-nona-2E,4E,8E/Z-trienamide mp 105°–15° C.

EXAMPLE 5

N-Isobutyl-7-phenylhept-2E-enamide

The product of Example 1 (100 mg) was dissolved in dry methanol (3 ml), 5% Pd/C (25 mg) was added, and the mixture was hydrogenated at atmospheric pressure and room temperature. The reaction mixture was diluted with methanol and filtered. The solvent was removed in vacuo, and ether was added then removed in a stream of nitrogen. The last traces of solvent were removed in vacuo to yield N-isobutyl-7-phenylhept-2E-enamide (68 mg). Refractive index 1.39.

EXAMPLE 6

N-Isobutyl-9-phenylnona-2E,4E-dien-8-ynamide (a) 5-Phenylpent-4-ynal (0.5 g) in $CH_2Cl_2$ (5 ml) was added to a solution of formylmethylenetriphenyl phosphorane (1.8 g) in $CH_2Cl_2$ (10 ml) and the mixture was stirred at room temperature under a dry nitrogen atmosphere for 24 hours. The solvent was removed under reduced pressure and the residue was slurried with ether (50 ml), filtered, and the residue washed with ether. The ethereal solutions were combined and the product was purified by chromatography on silica eluting with ether:hexane (1:9) to yield 7-phenylhept-2E-en-6-ynal (0.25 g) as a yellow oil.

(b) Chloroacetyl chloride (37.58 g) was added dropwise over 1 hour to a solution of isobutylamine (46.8 g) in ether (500 ml) maintaining the temperature below 5° C. Water (100 ml) was then added, and the organic layer was separated and washed with dilute hydrochloric acid, sodium hydroxide, and brine and dried (MgSO4). The solvent was removed in vacuo to yield N-isobutylchloroacetamide (47 g).

(c) The product from (b) above converted to isobutylaminocarbonylmethyltriphenylphosphonium chloride by reaction with triphenylphosphine (82 g) in benzene (600 ml) at reflux temperature for 75 hours. The product was isolated by filtration and dried in vacuo.

(d) The product from (C) above (1.24 g) in methanol, sodium methoxide in methanol (1.53 ml; 1.14 g/30 ml) and the product from (a) above (0.4 g) were allowed react together. The reaction mixture was worked up as described in Example 1 and purified by chromatography on silica, eluting with ether:hexane (1:1) grading to ether, to yield N-isobutyl-9-phenylnona-2E,4E-dien-8-ynamide (90 mg).

EXAMPLE 7

N-(3-Methoxybenzyl)-7-phenylhept-2E-en-6-ynamide 7-phenylhept-2E-en-6-ynoic acid (100 mg) was converted to the acid chloride as described in Example 2(a). The acid chloride was treated with triethylamine (73 ul) and 3-methoxybenzylamine (77 ul) in ether (2 ml). The product was recovered as described in Example 1 and purified by chromatography on silica, eluting with ether:hexane (1:1) to yield N-(3-methoxybenzyl)-7-phenylhept-2E-en-6-ynamide as a colourless solid, m.p. 96.3°–98.9°.

EXAMPLE 8

N-Isobutyl-9-phenylnona-2E-en-6,8-diynamide (a) A solution of sodium hydroxide (31.4 g) in water (160 ml) was cooled to 6° C. and bromine (18 ml) was added dropwise, the temperature being kept below 20° C. Phenylacetylene (20 g) in dimethoxyethane (80 ml) was added over 15 minutes and the mixture was stirred at room temperature for 5 hours. Water (200 ml) was added, and the mixture was extracted with ether (4×60 ml), dried (MgSO4) and the solvents removed at room temperature to yield phenylbromoacetylene.

(b) To a mixture of tetrahydrofurfuryl alcohol (408 g) and pyridine (348 ml) was added thionyl chloride, keeping the temperature below 60° C., and the mixture was maintained at room temperature overnight. The mixture was extracted with ether (6×600 ml) and the extracts were washed with water (4×100 ml) and dried (Na2SO4/MgSO4). The solvent was removed in vacuo and the residue distilled at reduced pressure to yield tetrahydrofurfuryl chloride.

(c) Sodium (40.5 g) was added in 1 g pieces to a mixture of ferric nitrate hydrate (0.6 g) and anhydrous liquid ammonia (11), followed by the addition of tetrahydrofurfuryl chloride (60 g). The mixture was stirred for 1 hour and solid ammonium chloride (80 g) was added cautiously over 20 minutes. The ammonia was allowed to evaporate and the residue was extracted with ether (10×100 ml). The extracts were combined and concentrated in vacuo, then distilled at reduced pressure to yield pent-4-yn-1-ol.

(d) 70% aqueous ethylamine (8 ml) was added to a mixture of methanol (20 ml), cuprous chloride (0.25 g), hydroxylamine hydrochloride (0.5 g) and pent-4-yn-1-ol (5 g), followed by water (80 ml). The mixture was warmed to 35° C., and phenylbromoacetylene (9.5 g) was added over 20 minutes under a nitrogen atmosphere.

The mixture was stirred at 35° C. for 40 minutes, then sodium cyanide (0.5 g) was added. The mixture was poured on to ice, then allowed to warm to room temperature and filtered. The solid product was washed with water, dried in vacuo and purified by silica chromatography, eluting with ether:hexane (1:1) to yield 7-phenylhepta-4,6-diyn-1-ol (6 g), m.p. 50.9°–51.6° C.

(e) The alcohol from (d) above (4.2 g) in CH2Cl2 (25 ml) was added to pyridinium chlorochromate (8.4 g) in CH2Cl2 (35 ml). The mixture was kept at room temperature for 2.5 hours and worked up as described in Example 1(c) to yield 7-phenylhepta-4,6-diynal (3.6 g) as a yellow-brown oil.

(f) Using the process described in Example 6(d), the aldehyde from (e) above (0.6 g) was converted to N-isobutyl-9-phenylnona-2E-en-6,8-diynamide (0.36 g) m.p. 133.8°–135.2° C.

EXAMPLE 9

N-isobutyl-9-phenyl-nona-2E,6Z,8Etrienamide (a) Cuprous iodide (0.4 g, 2.1 mmol) and bis-triphenylphosphine palladium (II) chloride (0.8 g, 1.14 mmol) were added to a solution of pent-4-yn-1-ol (16 g, 193 mmol) (Jones, Eglinton, and Whiting, Org. Syn. Coll., 4, 755, (1963)) and E-styryl bromide (34.34 g, 188 mmol) (Feuerstein and Heimann, Ber., 34, 1468 (1901)) in anhydrous diethylamine (250 ml). The whole was stirred under an atmosphere of dry nitrogen with the exclusion of moisture and light for 16 hours. The diethylamine was removed at reduced pressure and the residue diluted with water (500 ml). The aqueous mixture was extracted with ether. The ethereal extracts were passed down a column composed of silica (100 g), Celite (trade name, from Koch-light Ltd) (100 g) and activated charcoal (20 g) at 3 psi (21 KPa) pressure. The column was washed with ether (200 ml) and the combined organic extracts dried over anhydrous magnesium sulphate. Removal of solvents gave 30.5 g of 7-phenyl-hept-4-yn-6E-en-1-ol as a pale brown oil. The material was not purified further.

Nuclear magnetic resonance spectra (NMR) were as follows: $^1$H(ppm from TMS in CDCl3, integral, number of peaks, $J_{Hz}$, assignment): 7.28, 5H, m, aromatic; 6.88, 1H, d, $J_{7,6}=16$, H7; 6.12, 1H, d, $J_{6,7}=16$, H6; 3.78, 2H, t, $J_{1,2}=6$, H1; 2.50, 2H, t, $J_{3,2}=7$, H3; 1.93, 1H, s, OH; 1.83, 2H, m, H2.

(b) Pyridinium chlorochromate (7 g, 325 mmol) was added in two portions to a cooled solution of 7-phenyl-hept-4-yn-6Een-1-ol (29 g, 156 mmol) in dry dichloromethane (750 ml) containing anhydrous sodium acetate (12 g, 146 mmol). The dark mixture was stirred at room temperature for 3 hours, and diluted with ether (1 L). The oily black residue was extracted with ether until granular. The combined organic extracts were passed down a column composed of silica (100 g), Celite (trade name, from Koch-light Ltd) (100 g) and activated charcoal (20 g) at 3 psi (21 KPa) pressure. The combined eluant was washed with satd. aqueous sodium bicarbonate, 2N aqueous hydrochloric acid and brine and dried over anhydrous magnesium sulphate. The solvents were removed to give 28.7 g (89% of theory) of 7-phenyl-hept-4-yn-6E-en-1-al as a red-brown oil.

(c) To a solution of triphenylphosphine (229.8 g, 876 mmol) in dry benzene (800 ml) was added N-isobutyl-2-chloroacetamide (131 g, 876 mmol) (prepared by standard methods from 2-chloroacetyl chloride and isobutylamine) in dry benzene (100 ml). The solution was heated under reflux, with vigorous stirring, for 8 hours. Upon cooling, colourless needles formed. These were collected by filtration and the filtrate heated under reflux for a further 8 hours. A second batch of the produce was collected. The combined batches were washed with dry ether and dried in vacuo to give 310 g (86% of theory) of N-isobutyl-acetamidotriphenyl-phosphonium chloride as colourless needles.

Nuclear magnetic resonance spectra (NMR) were as follows: $^1$H(ppm from TMS in CDCl$_3$, integral, number of peaks, $J_{Hz}$, assignment): 7.75, 15H, m, aromatic; 5.10, 2H, d, $J_{2,P}=15$, H2; 2.87, 2H, 2d, isobutyl CH$_2$; 1.55, 1H, m, isobutyl CH; 0.88, 6H, d, isobutyl methyls.

(d) Sodium methoxide (5.4 g, 100 mmol) in anhydrous methanol (127 ml) was added to a solution of N-isobutyl-acetamidotriphenylphosphonium chloride (52 g, 126 mmol) in anhydrous methanol (250 ml). The mixture was stirred at room temperature under an atmosphere of dry nitrogen for 4 hours. 7-phenyl-hept-4-yn-6E-en-1-al (17 g, 92 mmol) in anhydrous methanol (250 ml) was added over 20 mins. The mixture was stirred at room temperature under dry nitrogen for 16 hours. The methanol was removed at reduced pressure and the residue diluted with water. The aqueous emulsion was extracted with ether and the organic extracts washed with brine and dried over anhydrous magnesium sulphate.

The solvents were removed and the crude product purified first by dry column chromatography (silica, 1:1 ether/hexane ether) and then by recrystallisation (1:1 ethyl acetate/60°–80° petrol-ether) to give 6.62 g (25.5% of theory) of N-isobutyl-9-phenyl-nona-6-yn-2(E),8(E)-dienamide as colourless crystals.

Gas-liquid chromatography (g.l.c.): OV210 Δ 250° produced one peak.

Nuclear magnetic resonance spectra (NMR) were as follows: $^1$H(ppm from TMS in CDCl$_3$, integral, number of peaks, $J_{HZ}$, assignment): 7.33, 5H, s, aromatic; 7.02, 1H, m, H3; 6.90, 1H, d, $J_{9,8}=16$, H9; 6.13, 1H, d, $J_{8,9}=16$, H8; 6.03, 1H, NH; 5.92, 1H, d, $J_{2,3}=15$, H2; 3.17, 2H, 2d, isobutyl CH$_2$; 2.45, 4H, m, H4, H5; 1.81, 1H, m, isobutyl CH; 0.95, 6H, d, isobutyl methyls.

Mass spectrum (ms), chemical ionisation: m+1, 282.

(e) Lindlar catalyst (Pd-CaCO$_3$-PbO) (40 mg) was added to a solution of N-isobutyl-9-phenyl-nona-6-yn-2(E),8(E)-dienamide (2 g, 7.11 mmol) and synthetic quinoline (0.5 g) in dry ethyl acetate (70 ml). The mixture was subjected to hydrogenation at 1 atm (101 KPa) pressure. The reaction was halted at 99% of theoretical uptake (173 ml). The reaction mixture was diluted with ether (200 ml). The organic solution was washed in aqueous hydrochloric acid with saturated aqueous sodium bicarbonate and brine and dried over anhydrous magnesium sulphate. The solids were removed by filtration and the solvents removed from the filtrate to give a yellow oil which crystallised on standing at 5° C. The crude material was dissolved in the minimal quantity of ether and tritiated with 60°/80° petrol-ether. The colourless product was collected by filtration, a second crop being obtained from the filtrate. The combined products were dried in vacuo to give 1.59 g (80% of theory) of N-isobutyl-9-phenyl-nona-2(E),6(Z),8(E)-trienamide as very pale cream crystals, m.p. 62°.

Thin layer chromatography (t.l.c.): silica gel F254 plates/ether, R$_f$ 0.44 (lined tank). Gas liquid chromatography (g.l.c.): OV210 at 230° C., 95% pure.

Nuclear magnetic resonance spectra (NMR): $^{13}$C (90 MHz) (ppm from TMS in CDCl$_3$, assignment); 165.88, C1; 143.03, alkenyl; 137.49, Cl$^1$, phenyl, 132.86, 130.94, 129.63, 127.52, 124.51, 124.01, 5 alkenyls and 1 phenyl; 128.58, 126.39, 4 phenyls; 46.90, isobutyl C1; 32.01, C4; 28.59, isobutyl C2; 26.75, C5:20.08, isobutyl methyls. $^1$H(360 MHz) (ppm from TMS in CDCl$_3$, integral, number of peaks, $J_{HZ}$, assignment): 7.42, 2H, m, aromatic; 7.32, 2H, m, aromatic; 7.23, 1H, m, aromatic; 7.03, 1H, d of d, $J_{8,9}=15(E)$, $J_{8,7}=12$, H8; 6.84, 1H, d of t, $J_{3,2}=16(E)$, $J_{3,4}=6$, H3; 6.55, 1H, d, $J_{9,8}=15(E)$, H9; 6.20, 1H, d of d, $J_{7,6}=10(Z)$, $J_{7,8}=12$, H7; 5.81, 1H, d, $J_{2,3}=16(E)$, H2; 5.52, 1H, d of t, $J_{6,7}=10(Z)$, $J_{6,5}=7$, H6; 4.96, 1H, NH; 3.13, 2H, d of d, isobutyl CH$_2$; 2.31, 2H, m and 2.44, 2H, m, H4 and H5; 1.78, 1H, sept, isobutyl CH; 0.91, 6H, d, isobutyl methyls.

Coupling assignments were based upon spin decoupling experiment. Mass spectrum (m.s.), chemical ionisation: m+1, 284.

EXAMPLE 10

N-isobutyl-11-(3′-trifluoromethylphenyl)-2E,4E,8Z,-10E)-undecatetrenamide (a) A mixture of 3-(trifluoromethyl) benzaldehyde (25 g, 144 mmol), malonic acid (28.8 g, 277 mmol), anhydrous pyridine (100 ml) and piperidine (2 ml) was heated under reflux for 4 hours. The mixture was poured onto fresh ice (300 g) and concentrated hydrochloric acid (78 ml). The solid product was collected, dried and recrystallised (1:1 IMS/water) to give 30 g (96% of theory) of 3-(trifluoromethyl) cinnamic acid as off-white needles.

(b) Bromine (22.5 g, 141 mmol) was added dropwise to a solution of the 3-(trifluoromethyl) cinnamic acid (30 g, 138 mmol) and 2,2′-azobis-(2-methylpropionitrile) (0.4 g) in chloroform (1 L) under irradiation from a powerful lamp. The solution was heated under gentle reflux for 4 hours. The solvent was removed and the residue crystallised upon standing to give 49.3 g (94% of theory) of 2,3-dibromo-3-(3′-trifluoromethylphenyl) propionic acid. The material was not purified further.

(c) Sodium carbonate (44.1 g, 416 mmol) was added to a suspension of the 2,3-dibromo-3-(3′-trifluoromethylphenyl) propionic acid (49 g, 130 mmol). The mixture was heated under reflux for 6 hours. The mixture was allowed to cool and extracted with ether. The ethereal extracts were washed with aqueous sodium carbonate and brine and dried over anhydrous magnesium sulphate. The solvent was removed to give 14.8 g (45% of theory) of 1-bromo-3-(3-trifluoromethyl)-(E)-1-propene as a light brown oil.

(d) 4-pentyn-1-ol (4.3 g, 51.8 mmol) (prepared as in Example 9) and the 1-bromo-3-(3′-trifluoromethyl)-(E)-1-propene (14 g, 55.8 mmol) were used with the same method as for 7-phenyl-6E-hepten-4-yn-1-ol (Example 9), to give 7.83 g (56% of theory) of 7-(3-trifluoromethylphenyl)-6E-hept-4-yn-1-ol. Nuclear magnetic resonance spectrum (NMR): 7.50,4H,m aromatic; 6.92,1H,d,$J_{7,6}=16$,H7; 6.21,1H d of t, $J_{6,7}=16$; 3.83,2H,t,$J_{1,2}=6$,H1; 2.57,2H,t,$J_{3,2}=6$,H3; 2.08,1H,s,OH; 1.82,2H,m,H2.

(e) 7-(3′-trifluoromethylphenyl)-6E-hepten-4-yn-1-al was prepared from the 7-(3′-trifluoromethylphenyl)-6E-hepten-4-yn-1-ol (4 g, 15.75 mmol) using the same method as for 7-phenyl-6E-hepten-4-yn-1-ol (Example 9).

(f) A solution of the 7-(3′-trifluoromethylphenyl)-6E-hepten-4-yn-1-ol (3.97 g, 15.4 mmol) and carboethoxymethylene triphenylphosphorane (6.41 g, 18.4 mmol) in dry dichloromethane (60 ml) was stirred at room temperature under dry nitrogen for 16 hours. The solvent was removed at reduced pressure and the residue extracted with ether:hexane (1:1). The solvents were removed and the crude product purified by dry column chromatography (silica, 1:4 ether:hexane) to give 2.24 g (45% of theory) of ethyl 7-(3'-trifluoromethylphenyl)-(2E,8E)-nonadien-6-ynoate.

Nuclear magnetic resonance spectrum (NMR): 7.33,4H,m, aromatic; 7.0,1H[m,H3; 6.73,1H[d,$J_{9,8}$=16,H9; 6.13,1H,d,$J_{8,9}$=16,H8; 5.88,1H,d,$J_{2,3}$=15,H2; 4.21,2H,q,ethyl; 2.58,4H,m,H4,H5; 1.34,3H,t,ethyl.

(g) Diisobutylaluminium hydride in hexane (12 mmol) was added over 10 minutes at $-15°$ under dry nitrogen to a solution of ethyl 7-(3'-trifluoromethylphenyl)-(2E,8E)-nonadien-6-ynoate (2 g, 6.2 mmol) in dry dichloromethane (30 ml). The mixture was stirred at 0° for 3.5 hours and quenched with saturated aqueous ammonium chloride (30 ml) and 2N hydrochloric acid (30 ml). The organic phase was diluted with ether, separated, washed with aqueous sodium bicarbonate and brine and dried over magnesium sulphate. The solvents were removed and the crude product purified by dry column chromatography (silica, 1:9-1:1 ether:hexane) to give 1.02 g (58% of theory) of 7-(3'-trifluoromethylphenyl)-(2E,8E)-nonadien-6-yn-1-ol.

(h) 9-(3'-trifluoromethylphenyl)-(2E,8E)-nonadien-6-yn-1-al was prepared from 9-(3'-trifluoromethylphenyl)-(2E,8E)-nonadien-6-yn-1-ol (1 g, 3.57 mmol) using the same method as for 7-(3'-trifluoromethylphenyl)-6E-hepten-4-yn-1-al.

(i) The 9-(3'-trifluoromethylphenyl)-(2E,8E)-nonadien-6-yn-1-al (1.0 g, 3.6 mmol) and N-isobutyl acetamidotriphenyl phosphonium chloride (2.37 g, 5.75 mmol) were used with the same method as for N-isobutyl-9-phenyl-(2E,8E)-nonadien-6-ynamide (Example 9) to give N-isobutyl-11-(3'-trifluoromethylphenyl)-(2E,4E,10E)-undecatrien-8-ynamide (0.3 g, 23% of theory).

Nuclear magnetic resonance spectrum (NMR): 7.39,5H,m, aromatic and H3; 6.18,1H,d,$J_{11,10}$=16,H11; 6.18,4H,m,H4,5,10,NH; 5.87,1H,d,$J_{2,3}$=15,H2; 3.12,2H,d of d, isobutyl; 2.41,4H,m,H6,H7; 1.75,1H,m, isobutyl; 0.92,6H,d, isobutyl.

Mass spectrum (ms) chemical ionisation: m+1, 376.

(j) N-isobutyl-11-(3'-trifluoromethylphenyl)-(2E,4E,8Z,10E)-undecatetrenamide was prepared from N-isobutyl-11-(3'-trifluoromethylphenyl)-(2E,4E,10E)-undecatrien-8-ynamide (100 mg, 0.267 mmol) by semi-hydrogenation in the presence of Lindlar catalyst (18 mg) and quinoline (25 mg) in ethyl acetate (3 ml) using the same method as in Example 9. The crude product was purified by dry column chromatography (silica, 1:1 ether:hexane) to give 90 mg (89% of theory) of N-isobutyl-11-(3'-trifluoromethylphenyl)-(2E,4E,8Z,10E)-undecatetrenamide.

Thin layer chromatography (tlc): silica gel F254 plates/ether, $R_f$ 0.39 (lined tank). High pressure liquid chromatography (hplc): $C_8$-reverse phase/3:1 methanol:water at 10 ml min$^{-1}$ at 2200 psi (15 170 kPa), retention time 76 mins.

Nuclear magnetic resonance spectrum (NMR): 7.49,4H,m, aromatic; 7.40,1H,m,H3; 7.05,1H,m,H9; 6.73,1H,d,$J_{11,10}$=16,H11; 6.17,5H,m,H4,5,8,10,NH; 5.82,1H,d,$J_{2,3}$=15,H2; 3.24,2H,d of d, isobutyl; 2.34,4H,m,H6,H7; 1.68,1H,m, isobutyl; 0.92,6H,d, isobutyl.

EXAMPLE 11

N-isobutyl-13-phenyl-2E,4E,10Z,12E-tridecatetrenamide (a) 3-heptyn-1-ol (9 g, 80.4 mmol) was added, with cooling, to potassium 3-amino-propylamide, prepared from potassium hydride (1.07 g, 26.8 mmol) in 1,3-diaminopropane (25 ml). The mixture was stirred at room temperature under dry nitrogen for 16 hours. The mixture was washed with hexane and the upper layer discarded. The lower layer was quenched with brine and the aqueous emulsion washed with pentane. The aqueous phase was extracted exhaustively with ether and the organic phase washed with 2N hydrochloric acid, aqueous sodium bicarbonate and brine and dried over magnesium sulphate. The solvents were removed to give 4.4 g (49% of theory) of 6-heptyn-1-ol as a pale yellow liquid. The material was used without further purification.

(b) 9-phenyl-8E-nonen-6-yn-1-ol was prepared from the 6-heptyn-1-ol (3.1 g) and (E)-styryl bromide (7 g) in dry diethylamine (40 ml) in the presence of bis-triphenyl phosphine palladium (II) chloride (0.23 g) and cuprous iodide (0.09 g), using the same method as in Example 9, to give 4 g (68% of theory) of 9-phenyl-8E-nonen-6-yn-1-ol as a pale yellow oil.

Nuclear magnetic resonance spectrum (NMR): 7.23,5H,m, aromatic; 6.78,1H,d,$J_{9,8}$=16,H9; 6.01,1H,d of t,$J_{8,9}$=16,H8; 3.58,2H,m,H1; 2.54,1H,s,OH; 2.33,2H,m,H5; 1.56,6H,m,H2,3,4.

(c) 9-phenyl-8E-nonen-6-yn-1-al was prepared from the 9-phenyl-8E-nonen-6-yn-1-ol (4 g, 18.7 mmol) using the same method as in Example 9. The crude product was purified by flash-column chromatography (40–63 silica $\Delta$ 3 psi (20 kPa) of nitrogen, 3:7 ether:hexane) to give 2.5 g (64% of theory) of 9-phenyl-8E-nonen-6-yn-1-al as a yellow oil.

(d) Ethyl 11-phenyl-(2E,10E)-undecadien-8-ynoate was prepared from the 9-phenyl-(8E)-nonen-6-yn-1-al (2.5 g) using the same method as in Example 10 to give 3 g (90% of theory) of ethyl 11-phenyl-(2E,10E)-undecadien-8-ynoate as a colourless oil.

(e) 11-phenyl-(2E,10E)-undecadien-8-yn-1-ol was prepared from ethyl 11-phenyl-(2E,10E)-undecadien-8-ynoate (2.9 g, 10.4 mmol) using the same method as in Example 10 to give 2.6 g (99% of theory) of 11-phenyl-(2E,10E)-undecadien-8-yn-1-ol as a yellow oil.

Nuclear magnetic resonance spectrum (NMR): 7.23,5H,m, aromatic; 6.85,1H,d,$J_{11,10}$=16,H11; 6.1,1H,d of t,$J_{10,11}$=16,H10; 5.65,2H,m,H2,3; 4.07,2H,m,H1; 2.20,4H,m,H4,7; 1.59,4H,m,H5,6.

(f) 11-phenyl-(2E,10E)-undecadien-8-yn-1-al was prepared from 11-phenyl-(2E,10E)-undecadien-8-yn-1-ol (2.5 g, 10.33 mmol) using the same method as in Example 9.

(g) N-isobutyl 13-phenyl-(2E,4E,12E)-tridecatrien-1-ynamide was prepared from the 11-phenyl-(2E,10E)-undecadien-8-yn-1-al (2.5 g, 10.3 mmol) using the same method as in Example 9 to give N-isobutyl 13-phenyl(-2E,4E,12E)-tridecatrien-10-ynamide 0.2 g (6% of theory) as pale yellow crystals.

Thin layer chromatography (tlc): silica gel F254 plates/ether, $R_f$ 0.47 (lined tank). Gas liquid chromatography (glc): OV210 $\Delta$ 275°, 95% pure.

Nuclear magnetic resonance spectrum (NMR): 7.22,5H,m, aromatic; 7.07,1H,m,H3; 6.78,2H,d,$J_{13,12}$=16,H13; 6.53,1H,NH:

6.12,3H,m,H4,5,12; 6.87,1H,d,J$_{2,3}$=15,H2;3,10,2H,d of d, isobutyl; 2.25,4H,m,H6,9; 1.60,5H,m,H7,8 and isobutyl; 0.94,6H,d, isobutyl.

(h) Finally, N-isobutyl 13-phenyl-(2E,4E,10Z,12E)-tridecatetrenamide was prepared from 13-phenyl-(2E,4E,12E)-tridecatrien-10-ynamide (80 mg, 0.24 mmol) using the same method as Example 9 to give 61 mg (75% of theory) of pale yellow crystals.

Thin layer chromatography (tlc): silica gel F254 plates/ether, R$_f$ 0.47 (lined tank). High pressure liquid chromatography (hplc): C$_8$ reverse phase/80% methanol, 20% water Δ 10 ml.min$^{-1}$, retention time 50 mins.

Nuclear magnetic resonance spectrum (NMR): 7.26,5H,m, aromatic; 7.00,2H,m,H3,H11; 6.70,1H,d,J$_{13,12}$=16,H13; 6.08,5H,m,H4,5,10,12,NH; 3.13,2H,d of d, isobutyl; 2.24,4H,m,H6,H9; 1.50,5H,m,H7,H8, isobutyl; 0.93,6H,d, isobutyl.

EXAMPLE 12

N-isobutyl 7-phenyl-6-E,Z-heptenamide (a) A solution of N-isobutyl 6-bromohexamide (3 g, 12.7 mmol) was prepared from 6-bromohexanoyl chloride and an excess of isobutylamine in dry ether and triphenylphosphine (4 g, 15.3 mmol) in dry xylene was heated under reflux for 6 hours. The solvent was removed, the residue dissolved in chloroform and the solution was added dropwise to dry ether. The oily solid was kept at 0° C. for 3 days, collected and dried in vacuo to give 6.5 g (95% of theory) of N-isobutyl 6-triphenylphosphoniumhexamido bromide, which was used without further purification.

(b) To a solution of sodium methoxide (from 6.08 mmol of sodium) in dry dimethylformamide (2 ml) was added the N-isobutyl 6-triphenyl/phosphonium-hexamido bromide (4 g, 6.3 mmol) in dry dimethyl/formamide (8 ml). After 3 hours at room temperature, benzaldehyde (0.5 g, 4.7 mmol) was added and the mixture stirred at room temperature under nitrogen for 24 hours. The reaction mixture was diluted with water and extracted with benzene. The organic extracts were dried and the solvent removed to give a crude product which was purified by dry column chromatography, (silica/ether) to give 0.8 g (65% of theory) of N-isobutyl 7-phenyl 6E,Z-heptenamide (69% Z, 31% E) as a colourless oil.

Nuclear magnetic resonance (NMR): 7.23,5H,m, aromatic; 6.39,1H,m,H7; 5.59,1H,m,H6; 3.06,2H,d of d, isobutyl; 2.20,4H,m,H2,5; 1.64,H,m,H3,4, isobutyl; 0.93,6H,d, isobutyl.

EXAMPLE 13

N-isobutyl 2-methyl-7-phenyl-2E,6Z-heptadienamide (a) 5-phenyl-pent-4-yn-1-al (1 g, 6.33 mmol) (Example 1) and carboethoxymethylmethylene triphenylphosphorane were used with the same method as in Example 1 to give 1.5 g (98% of theory) of ethyl 2-methyl-7-phenyl-(2E)-hepten-6-ynoate as a pale yellow oil.

(b) The ethyl 2-methyl-7-phenyl-(2E)-heptene-6-ynoate (1.0 g, 4.13 mmol), ethanol (4 ml), potassium hydroxide (1 g) and water (4 ml) were heated together under a nitrogen atmosphere at 50° C. for 2 hours. The reaction mixture was worked up as in Example 1 to give 0.84 g (95% of theory) of 2-methyl-7-phenyl-(2E)-hepten-6-ynoic acid as a colourless solid.

(c) 2-Methyl-7-phenyl-(2E)-hepten-6-ynoic acid with the same method as in Example 2 gave 0.62 g (65% of theory) of N-isobutyl 2-methyl-7-phenyl-(2E)-heptene-6-ynamide as colourless crystals.

(d) Semi-hydrogenation of N-isobutyl 2-methyl-7-phenyl-(2E)-heptene-6-ynamide (0.1 g, 0.37 mmol) in the presence of Lindlar catalyst and quinoline, using the same method as Example 9, gave 100 mg (98% of theory) of N-isobutyl 2-methyl-7-phenyl-(2E,6Z)-heptadienamide.

Nuclear magnetic resonance (NMR): 7.26,5H,m, aromatic; 6.38,2H,m,H3,7; 5.78,2H,m,H6,NH; 3.15,2H,d of d, isobutyl; 2.38,4H,m,H4,5; 1.83,3H,s,Me; 1.77,1H,m, isobutyl; 0.93,6H,d, isobutyl.

Mass spectrum (ms) chemical ionisation: m+1, 272.

EXAMPLE 14

N-isobutyl-2-bromo-7-phenyl-2E-hepten-6-ynamide (a) A solution of triphenylphosphine (33.8 g, 129 mmol) and t-butyl bromoacetate (25 g, 128.2 mmol) in dry benzene (150 ml) was stirred for 16 hours at room temperature. The precipitated product was collected by filtration, washed with dry ether and dried in vacuo to give 56 g (96% of theory) of carbo-t-butoxymethyl triphenylphosphonium bromide.

(b) A suspension of the carbo-t-butoxymethyl triphenylphosphonium bromide (55.8 g, 122 mmol) in water (400 ml) was treated with sodium hydroxide (4.7 g, 117 mml) in water (100 ml). The mixture was stirred for 16 hours and the solid collected to give 43.7 g (95% of theory) of carbo-t-butoxymethylene triphenylphosphorane.

(c) A solution of the carbo-t-butoxymethylene triphenylphosphorane (20 g, 57 mmol) in dry dichloromethane (500 ml) was treated with bromine (2.75 ml, 53 mmol) in carbon tetrachloride (60 ml) at −70° C. The mixture was allowed to reach room temperature and the solvents were removed. The residue was suspended in water (200 ml) and treated with 6% aqueous sodium hydroxide (36 ml). The mixture was stirred for 1.5 hours and the product collected by filtration to give 1-bromo-1-carbo-t-butoxymethylene triphenylphosphorane as a pale yellow solid.

(d) 5-phenyl-pent-4-yn-1-al (1.1 g, 7.0 mmol) (Example 1) and 1-bromo-1-carbo-t-butoxymethyylene triphenylphosphorane were used with the same method as in Example 1 to give 2.24 g (96% of theory) of t-butyl 2-bromo-7-phenyl-(2E)-hepten-6-ynoate as a pale yellow oil.

(e) A solution of t-butyl 2-bromo-7-phenyl-(2E)-hepten-6-ynoate (1.5 g, 4.48 mmol) and 4-toluenesulphonic acid (0.1 g) in dry benzene (15 ml) was heated under reflux under dry nitrogen for 2 hours. The cooled mixture was diluted with ether and the organic phase was extracted with aqueous sodium bicarbonate. The aqueous phase was acidified and extracted with ether. The organic phase was washed with brine and dried over magnesium sulphate. The solvents were removed to give 0.95 g (76% of theory) of 2-bromo-7-phenyl-(2E)-hepten-6-ynoic acid as a colourless solid.

(f) 2-bromo-7-phenyl-(2E)-hepten-6-ynoic acid (0.2 g, 0.72 mmol) and the same method as Example 2 then gave N-isobutyl 2-bromo-7-phenyl-(2E)-hepten-6-ynamide.

(g) From N-isobutyl 2-bromo-7-phenyl-(2E)-hepten-6-ynamide (40 mg, 0.12 mmol) the same method as Example 9 gave 30 mg (73% of theory) of N-isobutyl 2-bromo-7-phenyl-(2E,6Z)-heptadienamide.

Nuclear magnetic resonance spectrum (NMR): 7.26,6H,m, aromatic, NH; 6.57,2H,m,H7,3; 5.75,1H,m,H6; 3.18,2H,d of d, isobutyl; 2.51,4H,m H4,5; 1.80,1H,m, isobutyl; 0.95,6H,d, isobutyl.

Mass spectrum (ms), chemical ionisation: m+1, 336 and 334 (2 isotopes of bromine).

EXAMPLE 15

5-(2'-methylphenyl)-(2E,6Z)-6-heptadienamide (a) A mixture of 4-pentyn-1-ol (1 g, 12.1 mmol), 2-iodotoluene (2.53 g, 11.6 mmol), dry diethylamine (20 ml), bis-triphenyl-phosphine palladium (II) chloride (150 mg) and cuprous iodide (60 mg) was stirred at room temperature under dry nitrogen for 24 hours. The solvent was removed and the residue extracted with ether. The organic phase was washed with brine and dried and the solvent removed. The crude product was purified by dry column chromatography (alumina, 9:1 hexane:ether 1:1 hexane:ether) to give 1.2 g (60% of theory) of 5-(2'-methylphenyl)-4-pentyn-1-ol as a brown oil.

(b) 5-(2'-methylphenyl)-4-pentyn-1-al was then prepared from 5-(2'-methylphenyl)-4-pentyn-1-ol (1.20 g, 6.9 mmol) using the same method as in Example 9.

(c) 5-(2'-methylphenyl)-4-pentyn-1-al and N-isobutyl acetamidotriphenyl phosphonium chloride with the same method as in Example 9 gave 0.7 g (43% of theory) of N-isobutyl 7-(2'-methylphenyl)-(2E)-hepten-6-ynamide.

(d) Semi-hydrogenation of N-isobutyl 7-(2'-methylphenyl)-(2E)-hepten-6-ynamide as in Example 9, gave 60 mg (58% of theory) of N-isobutyl 7-(2'methylphenyl)-(2E,6Z)-heptadienamide.

Nuclear magnetic resonance spectrum (NMR): 7.09,5H,m, aromatic; 6.68,2H,m,H3,7; 5.9,2H,m,H6,NH; 5.74,1H,m,$J_{2,3}$=15,H2; 3.09,2H,d of d, isobutyl; 2.30,3H,s,Me; 4H,m,H4,5; 1.77,1H,m, isobutyl; 0.93,6H,d, isobutyl.

Mass spectrum (ms) chemical ionisation: m+1, 272.

EXAMPLE 16

N-isobutyl 7-(4'-methoxyphenyl)-(2E,6Z)-heptadienamide (a) 5-(4'-methoxyphenyl)-4-pentyn-1-ol was prepared from 4-pentyn-1-ol and 4-iodoanisole using the same method as in Example 15 to give 1.55 g (70% of theory) of product.

(b) 5-(4'-methoxyphenyl)-4-pentyn-1-al was then prepared from 5-(4'-methoxyphenyl)-4-pentyn-1-ol using the same method as in Example 9.

(c) 5-(4'-methoxyphenyl)-4-pentyn-1-al and N-isobutyl acetamidotriphenylphosphonium chloride by the same method as in Example 9 gave 210 mg (20% of theory) of N-isobutyl 7-(4'-methoxyphenyl)-(2E)-hepten-6-ynamide.

(d) Finally, Semi-hydrogenation of N-isobutyl 7-(4'-methoxyphenyl)-(2E)-hepten-6-ynamide as in Example 9 gave 97 mg (98% of theory) of N-isobutyl 7-(4'-methoxyphenyl)-(2E,6Z)-heptadienamide.

Nuclear magnetic resonance spectrum (NMR): 7.00,4H, AB quartet, aromatic; 6.75,1H,m,H3; 6.39,1H,d,$J_{7,6}$=10,H7; 6.05,1H,NH; 5.85,1H,d,$J_{2,3}$=15,H2; 5.73,1H,m,H6; 3.80,3H,s,OMe; 3.14,2H,d of d, isobutyl; 2.42,4H,m,H4,5; 1.80,1H,m, isobutyl; 0.97,6H,d, isobutyl.

Mass spectrum (ms), chemical ionisation: m+1, 288.

EXAMPLE 17

N-isobutyl 7-(4'-bromophenyl)-(2E,6Z)-heptadienamide (a) 4-bromophenylacetylene (10 g, 55 mmol), prepared according to *Organic Reactions* 5 (1), 50, (1949), in dry dimethyl sulphoxide (7.0 ml) was added to lithium amide (from 66 mmol) of lithium) in liquid ammonia (200 ml). The mixture was stirred for 1 hour at −30° C., 2-(2-bromoethyl)-1,3-dioxolane (10 g, 55 mmol) was added and the mixture was stirred for 2 hours at −30° C. Ammonium chloride (12 g) was added, the ammonia was allowed to evaporate and water (200 ml) was added to the residue. The emulsion was extracted with ether and the organic phase was washed with brine and dried. The solvents were removed and the product purified by dry column chromatography (silica, 5% ether in hexane 1:1 ether:hexane) to give 4.08 g (26% of theory) of 5-(4'bromophenyl)-4-pentyn-1-al ethylene acetal.

(b) A mixture of 5-(4'-bromophenyl)-4-pentyn-1-al ethylene acetal (1.25 g, 4.5 mmol) water (7.5 ml), acetone (8 ml) and concentrated hydrochloric acid (1 ml) was stirred for 24 hours under nitrogen. The reaction mixture was diluted with brine, extracted with ether and the organic phase washed with aqueous sodium bicarbonate and brine and dried. The solvents were removed and the product, 5-(4'-bromophenyl)-4-pentyn-1-al, used without further purification.

(c) N-isobutyl 7-(4'-bromophenyl)-(2E)-hepten-6-ynamide was prepared from 5-(4'-bromophenyl)-4-pentyn-1-al and N-isobutyl acetamidotriphenylphosphonium chloride as in Example 9 and semi-hydrogenated as in Example 9 to give N-isobutyl 7-(4'-bromophenyl)-(2E,6Z)-hepta-dienamide.

Nuclear magnetic resonance (NMR): 7.22,4H, AB quartet, aromatic; 6.73,1H,m,H3; 6.34,1H,d,$J_{7,6}$=10,H7; 3.12,1H,d of d, isobutyl; 2.34,4H,m,H4,5; 1.80,1H,m, isobutyl; 0.92,6H,d, isobutyl.

Mass spectrum (ms), chemical ionisation: m+1, 336, 338 (2 isotopes of bromine).

EXAMPLE 18

N-isobutyl 7-(4'-phenylphenyl)(2E,6Z)-heptadienamide 5-(4'-phenylphenyl)-4-pentyn-1-ol was prepared from 4-pentyn-1-ol and 4'-bromobiphenyl as in Example 15, and converted into 5-(4'-phenylphenyl)-4-pentyn-1-al by the method of Example 9. N-isobutyl 7-(4'-phenylphenyl)-(2E)-hepten-6-ynamide was then prepared from 5-(4'-phenylphenyl)-4-pentyn-1-pentyn-1-al and N-isobutylacetamidotriphenylphosphonium chloride as in Example 9 and semi-hydrogenated as in Example 9 to give N-isobutyl 7-(4'-phenylphenyl)-(2E,6Z)-heptadienamide.

Nuclear magnetic resonance spectrum (NMR): 7.41,9H,m, aromatic 6.80,1H,m,H3; 6.47,1H,d,$J_{7,6}$=10,H7; 5.80,1H,d,$J_{2,3}$=15,H2; 5.66,2H,m,H6,NH; 3.14,2H,d of d, isobutyl; 2.40,4H,m,H4,5; 1.73,1H,m, isobutyl; 0.94,6H,d, isobutyl.

Mass spectrum (ms), chemical ionisation: m+1, 334.

EXAMPLE 19

N-isobutyl 7-(3'-propenylphenyl)-(2E,6Z)-heptadienamide (a) 3-iodobenzaldehyde was prepared by oxidation of 3-iodobenzylalcohol by pyridinium chlorochromate in the presence of sodium acetate as in Example 9.

(b) A suspension of ethyltriphenylphosphonium bromide (8.2 g, 22 mmol) in dry tetrahydrofuran (25 ml) was treated with n-butyl lithium in hexane (21.1 mmol). The solution was cooled to −60° C. and treated with 3-iodobenzaldehyde (4.9 g, 21.1 mmol). The mixture was stirred for 18 hours at room temperature, treated with water and extracted into ether. The organic phase was washed with 2N hydrochloric acid, aqueous sodium bicarbonate and brine, dried and the solvents removed. The crude product was purified by dry column chromatography (silica, 1:1 ether:hexane) to give 4 g (76% of theory) of 3-(1'-propenyl)-iodobenzene.

(c) 5-(3'-propenylphenyl)-4-pentyn-1-ol was prepared from 4-pentyn-1-ol and 3-(1'-propenyl) iodobenzene as in Example 15 and converted into 5-(3'-propenylphenyl)-4-pentyn-1-al by the method of Example 9.

(d) N-isobutyl 7-(3'-propenylphenyl)-(2E)-hepten-6-ynamide was prepared from 5-(3'-propenylphenyl)-4-pentyl-1-al and N-isobutyl acetamidotriphenylphosphonium chloride as in Example 9 and semi-hydrogenated as in Example 9 to give N-isobutyl 7-(3'-propenylphenyl)-(2E,6Z)-heptadienamide.

Mass spectrum (ms), chemical ionisation; m+1, 298.

EXAMPLE 20

N-isobutyl 7-2'-(methyl 3-phenylacrylate)-2E-hepten-6-ynamide (a) 2-iodobenzaldehyde was prepared from 2-iodobenzylalcohol as in Example 9, and oxidised to the cinnamic acid derivative according to *Organic Reactions* 1$_2$(8), 256 (1942), the acid then being methylated to give methyl 2-iodo-cinnamate.

(b) 5-2'-(methyl-3-phenylacrylate)-4-pentyl-1-ol was prepared from 4-pentyn-1-ol and methyl 2-iodocinnamate as in Example 15 and converted into 5-2'-(methyl-3-phenylacrylate)-4-pentyn-1-al as in Example 9.

(c) Finally, N-isobutyl 7-2'-(methyl 3-phenylacrylate)-(2E)-hepten-6-ynamide was prepared from 5-2'-(methyl-3-phenylacrylate)-4-pentyn-1-al and N-isobutyl acetamidotriphenylphosphonium chloride as in Example 9.

Nuclear magnetic resonance spectrum (NMR): 8.18,1H,d,$J_{2,3}$=16,H2'; 7.36,4H,m, aromatic; 6.72,2H,m,H3,NH; 6.47,1H,d,$J_{3,2}$=16,H3'; 6.13,1H,d,$J_{2,3}$=16,H2; 3.82,3H,s,CO$_2$Me; 3.15,2H,d of d, isobutyl; 2.61,4H,m,H4,5; 1.82,1H,m, isobutyl; 0.95,6H,d, isobutyl.

EXAMPLE 21

N-isobutyl 7(3'-chloro-4'-fluorophenyl)-(2E,6Z)-heptadienamide (a) 5-(3'-chloro-4'-fluorophenyl)-4-pentyn-1-ol was prepared from 4-pentyn-1-ol and 3'-chloro-4'-fluoro-iodobenzene as in Example 15 and converted into 5-(3'-chloro-4'-fluorophenyl)-4-pentyn-1-al as in Example 9.

(b) N-isobutyl 7-(3'-chloro-4'-fluorophenyl)-2E)-hepten-6-ynamide was then prepared from 5-(3'-chloro-4'-fluorophenyl)-4-pentyn-1-al and N-isobutyl acetamidotriphenylphosphonium chloride as in Example 9. Semihydrogenation as in Example 9 gave the title product.

Nuclear magnetic resonance spectrum (NMR): 7.16,3H,m, aromatic; 6.71,1H,m,H3; 6.34,1H,d,$J_{7,6}$=10,H7; 6.05,1H,NH; 5.86,1H,d,$J_{2,3}$=14,H2; 5.60,1H,m,H6; 3.15,2H,d of d, isobutyl; 2.36,4H,m,H4,5; 1.80,1H, isobutyl; 0.94,6H,d, isobutyl.

Mass spectrum (ms), chemical ionisation: m+1, 310, 312 (2 isotopes of chlorine).

EXAMPLE 22

N-isobutyl 7-(2',3'-dichlorophenyl)-(2E,6Z)-heptadienamide (a) 5-(2',3'-dichlorophenyl)-4-pentyn-1-ol was prepared from 4-pentyn-1-ol and 2,3-dichloro-iodobenzene using the same method as in Example 15 and converted into 5-(2',3'-dichlorophenyl)-4-pentyn-1-al as in Example 9.

(b) N-isobutyl 7-(2',3'-dichlorophenyl)-(2E)-hepten-6-ynamide was then prepared from 5-(2',3'-dichlorophenyl)-4-pentyn-1-al and N-isobutyl acetamidotriphenylphosphonium chloride as in Example 9. Semi-hydrogenation as in Example 9 gave the title product.

Nuclear magnetic resonance spectrum (NMR): 7.22,4H,m, aromatic; 6.72,1H,m,H3; 6.53,1H,d,$J_{7,6}$=10,H7; 5.8,2H,m,H6,NH; 5.79,1H,d,$J_{2,3}$=15,H2; 3.13,2H,d of d, isobutyl; 2.30,4H,m,H4,5; 1.78,1H,m, isobutyl; 0.92,6H,d, isobutyl.

Mass spectrum (ms), chemical ionisation: m+1, 326, 328.

EXAMPLE 23

N-isobutyl 7-thienyl-(2E,6Z)-heptadienamide (a) 5-thienyl-4-pentyn-1-ol was prepared from 4-pentyn-1-ol and 2-iodothiophene as in Example 15 and converted into 5-thienyl-4-pentyn-1-al as in Example 9.

(b) N-isobutyl 7-thienyl-(2E)-hepten-6-ynamide was prepared from 5-thienyl-4-pentyn-1-al and N-isobutyl acetamidotriphenyl-phosphonium chloride as in Example 9 and then converted to the title product by semi-hydrogenation as in Example 9.

Nuclear magnetic resonance spectrum (NMR): 7.06,3H, thienyl; 6.72,1H,m,H3; 6.53,1H,d,$J_{7,6}$=10,H7; 6.28,1H,NH; 6.87,1H,d,$J_{2,3}$=15,H2; 5.57,1H,m,H6; 3.13,2H,d of d, isobutyl; 2.46,4H,m,H4,5; 7.19,1H,m, isobutyl; 0.95,6H,d, isobutyl.

Mass spectrum (ms), chemical ionisation: m+1, 264.

EXAMPLE 24

N-isobutyl 4-(3-phenyl-(2Z)-propenoxy)-(2E)-butenamide (a) 2-chloromethoxyethyl benzoate was prepared from 2-hydroxyethyl benzoate and paraformaldehyde in the presence of anhydrous hydrogen chloride.

(b) Butyl lithium in hexane (30 mmol) was added to phenylacetylene (3.29 ml, 30 mmol) in dry THF (20 ml) at −78° C. The mixture was allowed to reach room temperature, cooled to 78° C. and 2-chloromethoxyethyl benzoate (6.4 g 30 mmol) added. The mixture was kept at 0° C. for 24 hours, quenched with water and extracted into ether. The crude product obtained from the organic phase was treated with 8% sodium hydroxide in ethanol (100 ml) and heated under reflux for 0.5 hours. The crude product was poured into water and extracted into ether. The ether extracts were washed with water, dried and the solvent removed to give 5 g of 2-(3-phenyl-2-propynoxy) ethanol.

(c) 2-(3-phenyl-2-propynoxy) ethanal was then prepared by oxidation of 2-(3-phenyl-2-propynoxy) ethanol as in Example 1(c).

(d) N-isobutyl-4-(3-phenyl-2-propynoxy)-(2E)-butenamide was prepared from 2-(3-phenyl-2-propynoxy) ethanal and N-isobutyl acetamidotriphenylphosphonium chloride as in Example 9.

(e) Finally, N-isobutyl 4-(3-phenyl-(2Z)-propenoxy)-(2E)-butenamide was prepared from N-isobutyl 4-(3-phenyl-2-propynoxy)-(2E)-butenamide by semi-hydrogenation as in Example 9.

Nuclear magnetic resonance spectrum (NMR): 7.17,5H,m, aromatic; 6.65,2H,m,H3,3'; 5.95,3H,m,NH,H2,2'; 4.25,4H,m,H4,1'; 3.15,2H,d of d, isobutyl; 1.77,1H,m, isobutyl; 0.91,6H,d, isobutyl.

Mass spectrum (ms), chemical ionisation: m+1, 274.

EXAMPLE 25

N-isobutyl 6-methyl-7-phenyl-(2E,6E/Z)-heptadienamide (a) 5-acetoxy-2-pentanone was prepared from acetylacetone and 2-chloroethanol in the presence of sodium hydride and sodium iodide.

(b) Benzyl triphenylphosphonium chloride (51.9 g, 120 mmol) in dry dimethylformamide (200 ml) was treated with sodium hydride (120 mmol) at 0° C. The ylide was treated with the 5-acetoxy-2-pentanone and the mixture kept at room temperature under nitrogen for 24 hours. The mixture was worked-up in the conventional manner and the residue purified by dry column chromatography (silica, 15% ether/hexane) to give 5 g (19% of theory) of 1-phenyl-2-methyl-5-acetoxy-(1E/Z)-pentene.

(c) The product of step (b) was then hydrolysed with 8% sodium hydroxide in ethanol as in Example 24 to give 4-methyl-5-phenyl-(4E/Z)-penten-1-ol, which was oxidised as in Example 1(c) to give 4-methyl-5-phenyl-(4E/Z)-penten-1-al as in Example 1(c).

(d) Finally, 4-methyl-5-phenyl-(4E/Z)-penten-1-al and N-isobutyl acetamidotriphenylphosphonium chloride were treated as in Example 9 to the title product.

Nuclear magnetic resonance spectrum (NMR): 7.22,5H,m, aromatic; 6.73,1H,m,H3; 6.33,1H,t,H7; 5.85,2H,m,NH,H2; 3.15,2H,d of d, isobutyl; 2.35,4H,m,H4,5; 1.87,3H,t,Me; 1.75,1H,m, isobutyl; 0.94,6H,d, isobutyl.

Mass spectrum (ms), chemical ionisation: m+1, 272.

EXAMPLE 26

N-isobutyl 7-phenyl-(2E,6E/Z)-octadienamide (a) 6-acetoxy-2-hexanone was prepared from acetylacetone and 3-chloropropanol in the presence of sodium hydride and sodium iodide.

(b) The product of (a) (3 g, 20 mmol) in dry ether was treated with phenyl magnesium bromide (20 mmol). The mixture was stirred at 0° C. under nitrogen for 0.5 hours and heated under reflux for 0.5 hours. The cooled mixture was treated with ammonium chloride and worked up in conventional fashion. The crude product was purified by dry column chromatography (silica, 1:1 ether:hexane) to give 0.6 g (13% of theory) of 6-acetoxy-2-phenyl-hexane-2-ol as a colourless oil.

(c) The 6-acetoxy-2-phenyl-hexan-2-ol (0.4 g, 1.84 mmol), p-4-toluenesulphonic acid (0.1 g) and dry benzene (50 ml) were heated under reflux for 3 hours. The reaction mixture was worked-up and the crude product purified by dry column chromatography (silica, 9:1 hexane:ether). The resultant acetate was hydrolysed as in Example 24 to give 0.2 g of 5-phenyl-(4E/Z)-hexen-1-ol.

(d) 5-phenyl-(4E/Z)-hexen-1-al was prepared by oxidation of 5-phenyl-(4E/Z)4-hexen-1-ol as in Example 1(c).

(e) Finally, 5-phenyl-(4E/Z)-4-hexenal and N-isobutyl acetamidotriphenylphosphonium chloride were reacted as in Example 9 to give the title compound.

Nuclear magnetic resonance spectrum (NMR): 7.28,5H,m, aromatic; 6.87,1H,m,H3; 6.36,1H,NH; 5.89,1H,d,$J_{2,3}$=15,H2; 6.71,1H,m,H6; 3.15,2H,d of d, isobutyl; 2.13,4,H,m,H4,5; 2.00,3H,s,Me; 0.91,6H,d, isobutyl.

Mass spectrum (ms), chemical ionisation: m+1, 272

EXAMPLE 27

N-(7-phenyl-2E,6Z/E-heptadienoyl)piperidine (a) Butanedial was prepared from 2,5-diethoxytetrahydrofuran according to House et al, *J Org chem*, 30,1065 (1965) and converted into ethyl 5-formyl-(2E)-pentenoate according to House et al, *J Org Chem*, 30, 1065 (1965).

(b) Benzyltriphenylphosphonium chloride (2.49 g, 6.4 mmol) in dry THF (25 ml) was treated with n-butyl lithium in hexane (6.3 mmol). 5-Formyl-(2E)-pentenoate (1 g, 6.4 mmol) was added to the ylide and the mixture stirred for 18 hours at room temperature under nitrogen. The reaction was diluted with ether and filtered and the solvent was removed from the filtrate. The residue was purified by dry column chromatography (silica, 1:1 ether:hexane) to give 0.7 g (48% of theory) of ethyl 7-phenyl-(2E,6Z/E)-heptadienoate as a yellow oil.

(c) 7-phenyl-(2E,6Z/E)-heptadienoic acid was then prepared from the ethyl 7-phenyl-(2E,6Z/E)-heptadienoate as in Example 1 and converted into 7-phenyl-(2E,6Z/E)-heptadienoyl chloride according to Example 1(f).

(d) Finally, N-(7-phenyl-(2E,6Z/E)-heptadienoyl) piperidine was prepared from 7-phenyl-(2E,6Z/E)-heptadienoyl chloride and piperidine as in Example 1(f).

Nuclear magnetic resonance spectrum (NMR): 7.16,5H,m, aromatic; 6.68,1H,m,H3; 6.33,2H,m,H2,7; 5.58,1H,m,H6; 3.44,4H,m,NCH$_2$; 2.31,4H,m,H4,5; 1.53,6H,m, ring.

EXAMPLES 28-38

By methods of analogues to those of Example 1, and in particular Example 1(f), the following Compounds were made:

EXAMPLE 28

3,5-dimethyl-N-(7-phenyl-(2E,6Z/E)-heptadienoyl)-piperidine

Mass spectrum (ms), chemical ionisation: m+1, 298

EXAMPLE 29

N,N-diethyl 7-phenyl-(2E,6Z/E)-heptadienamide

Nuclear magnetic resonance (NMR): 7.28,5H,m, aromatic; 6.80,1H,m,H3; 6.37,2H,m,H7,2; 5.73,1H,m,H6; 3.40,4H,m,2NCH$_2$; 2.46,4H,m,H4,5; 1.18,6H,t, ethyl.

EXAMPLE 30

N-decyl 7-phenyl-(2E,6Z/E)-heptadienamide.

Nuclear magnetic resonance spectrum (NMR): 7.30,5H,m, aromatic; 6.72,1H,m,H3; 6.48,1H,m,H7; 5.75,3H,m,H2,6, NH; 3.12,2H,m,NHCH2; 2.41,4H,m,H4,5; 1.33,16H, chain; 0.97,3H,Me.

EXAMPLE 31

N-phenyl 7-phenyl-(2E,6Z/E)-heptadienamide

Mass spectrum (ms), chemical ionisation: m+1, 278.

EXAMPLE 32

N-(2-(3',4'-dimethoxyphenyl)ethyl)7-phenyl-(2E,6Z/E)-heptadienamide

Nuclear magnetic resonance spectrum (NMR): 7.19,5H,m, aromatic; 6.71,3H,m, aromatic; 6.58,1H,m,H3; 6.32,1H,m,H7; 5.77,1H,d,H2; 3.82,6H,s,OMe; 3.52,2H,m,NH,CH2; 2.78,2H,m, benzyl; 2.33,4H,m,H4,5.

EXAMPLE 33

N-cyclopropyl 7-phenyl-(2E,6Z/E)-heptadienamide

Nuclear magnetic resonance spectrum (NMR): 7.17,5H,m, aromatic; 1H, NH; 6.67,1H,m,H3; 6.33,1H,m,H7; 5.80,1H,d,H2; 5.52,1H,m,H6; 2.30,4H,m,H4,5; 0.74,1H,m, cyclopropyl; 0.58,4H,m, cyclopropyl.

EXAMPLE 34

N-methyl-N-(2-methylpropyl) 7-phenyl-(2E,6Z/E)-heptadienamide

Nuclear magnetic resonance spectrum (NMR): 7.16,5H,m, aromatic; 6.67,1H,m,H3; 6.42,1H,m,H7; 5.70,2H,m,H2,6; 2.80,3H,s, NMe; 2.60,4H,m,H4,H5; 1.52,3H,m,CH[CH2; 1.02,6H,m,2Me.

EXAMPLE 35

N-benzyl 7-phenyl-(2E,6Z/E)-heptadienamide

Nuclear magnetic resonance spectrum (NMR): 7.23,10H,s, aromatic; 6.45,3H,m,H3,7,NH; 5.70,1H,d,H2; 5.42,1H,m,H6; 4.21,2H,d, NHCH2; 2.34,4H,m,H4,5.

EXAMPLE 36

N-cyclohexylmethyl 7-phenyl-(2E,6Z/E)-heptadienamide

Mass spectrum (ms), chemical ionisation: m+1, 298

EXAMPLE 37

N-(1-methoxycarbonyl-2-methylpropyl)7-phenyl-(2E,6Z/E)-heptadienamide

Nuclear magnetic resonance spectrum (NMR): 7.19,5H,m, aromatic; 6.69,1H,m,H3; 6.46,2H,m,H7,NH; 5.83,1H,d,H2; 5.50,1H,m,H6; 4.61,1H,m, NH CH; 3.67,3H,s,OMe; 2.34,4H,m,H4,H5; 1.74,1H,m, CH; 0.93,6H,d,2Me.

EXAMPLE 38

N-(2-bromo-2-propenyl)7-phenyl-(2E,6Z/E)-heptadienamide

Nuclear magnetic resonance spectrum (NMR): 7.20, 5H, m, aromatic; 6.7, 2H, m, H3': CH2; 6.44, 1H, m, H7; 6.23, 1H, NH; 5.78, 3H, m, H2, 6: CH2; 4.10, 2H, d, NH, CH2; 2.33, 4H, m, H4, 5.

EXAMPLE 39

NN-Hexamethylene-9-phenylnona-2E,6Z,8E,-trienamide (a) Phenyl N-phenylphosphoramido chloridate (0.6 g, 2.23 mmol.) was added to a stirred solution of 9-phenylnona-2(E),8(E)-en-6-ynoic acid (0.5 g, 2.21 mmol.) in dry dichloromethane (20 ml) containing dry triethylamine (0.5 ml) under nitrogen. After stirring for 1 hour, hexamethyleneimine (0.22 g, 2.22 mmol) in dry dichloromethane (20 ml) containing dry triethylamine (0.5 ml) was added and the mixture stirred for 18 hours. The solution was diluted with ether (100 ml), washed with dilute hydrochloric acid (2M, 50 mls) followed by distilled water (2×50 ml), dried over anhydrous magnesium sulphate and evaporated down to give a pale yellow oil (0.86 g). This was purified by dry column chromatography (silica, 1:1:1 ether: hexane: ethyl acetate) to give 0.23 g (33% of theory) of N,N-hexamethylene-9-phenylnona-2E,8E-en-6-ynamide as a viscous yellow oil.

Gas-liquid chromatography (g.l.c.) OV210 at 250° C. produced one peak. Mass spectrum (m.s.), chemical ionisation M+1,308 Nuclear magnetic resonance (NMR) 7.3, 5H, 5, aromatic; 7.0, 6.7, 6.4, 6.2 and 5.95, 4H, s+m, H3, H9, H8, H2; 3.5, 4H, m, H4, H5; 2.5, 4H, m, 2CH2s; 1.6, 8H broad s, hexamethylene ring CH2's.

(b) The title compound was prepared from NN-hexamethylene-9-phenylnona-2E,8E-en-6-ynamide (100 mg, 0.33 mmol) by semi-hydrogenation in the presence of Lindlar catalyst (100 mg) in ethyl propionate (20 ml) using the same method as in Example 9. The crude product was purified by dry column chromatography (silica, 1:1:1 ether: ethyl acetate: hexane) to give 40 mg of the title compound as a pale yellow oil.

Gas-liquid chromatography (g.l.c.) OV210 250° C. - One main peak Mass spectrum (m.s.) chemical ionisation M+1,310.

EXAMPLE 40

N-isobutyl 9-phenyl-8-chloro-(2E,6Z,8E)-nonatrienamide (a) A solution of phenylacetylene (2 g) in dry tetrachloromethane was treated, under anhydrous conditions, with tellurium tetrachloride (5.4 g). The mixture was heated for 1 hour under reflux, the solvent removed, and a suspension of the residue in acetonitrile (30 ml) heated under relux for 2 hours with iodine (5.1 g). The product was worked up and purified by dry column chromatography to give 2.7 g (38% of theory) of 1-iodo-2-chloro-3-phenyl-(E)-1-propene as an orange oil. 7-phenyl-6-chloro-6E-hepten-4-yn-1-ol was prepared from the oil and 4-pentyn-1-ol using the same method as in Example 9a to give 1.4 g (62% of theory).

(b) Redistilled oxalyl chloride (0.64 ml, 7.1 mmol) in dichloromethane (25 ml) was treated with dimethyl sulphoxide (1 ml, 14.16 mmol) at −60° C. for 10 mins. 7-phenyl-6-chloro-6E-hepten-4-yn-1-ol (1.4 g, 6.4 mmol) was added followed, after 30 mins, by triethylamine (3.5 ml). The reaction mixture was brought to room temperature, worked up and the crude product purified by dry column chromatography to give 7-phenyl-6-chloro-6E-hepten-4-yn-1-al. The method of Example 9 was then used to give N-isobutyl 9-phenyl-8- chloro-(2E,8E)-nonadien-6-ynamide, 0.85 g (39% of theory) as off-white crystals.

Nuclear magnetic resonance spectrum (NMR): 7.32, 5H,m, aromatic; 6.77, 1H,m,H3; 5.97,3H,m,H2,H8NH; 3.15,2H,d.of d.,isobutyl; 2.53,4H,m,H4,H5; 1.76,1H,m,isobutyl;0.96,6H,d,isobutyl.

(c) N-isobutyl 9-phenyl-8-chloro-(2E,8E)-nonadien-6-ynamide was reduced under Lindlar conditions as in Example 10 to give starting material and N-isobutyl 9-phenyl-8-chloro-(2E,6Z,8E)-nonatrienamide.

Mass spectrum (MS) chemical ionisation m+1,318,320.

BIOLOGICAL ACTIVITY

EXAMPLE A

The activity of compounds of the invention against female *Musca domestica* (WRL strain), with and without pretreatment with a synergist, was demonstrated by application to the test insect of a solution of the compound under test in butanone. Where pretreatment with a synergist was used, the test compound was applied 1 hour after application of the synergist (6 μg piperonyl butoxide (PB) per insect). Knockdown was assessed after 1 hour, and mortality after 24 hours.

The results are shown below:

| Compound of Example No: | Amount applied (μg) | Synergist* None | PB |
|---|---|---|---|
| Example 3 | 6 | 2.5(5) | 95(90) |
| Example 9 | 6 | 0(95) | 100(100) |

PB alone has 0% mortality and 0% knockdown at 6 μg per fly.
*The figures represent percent mortality among the test insects, with the percent knockdown figures in parentheses.

EXAMPLE B

The activity of compounds of the invention against male *Blattella germanica* was demonstrated by exposure of the insect for 1 hour to a deposit of the compound under test and a synergist (piperonyl butoxide) in a 1:1 ratio on glass. Knockdown was assessed after 10 and 60 minutes and mortality after 1 and 6 days.

The results are shown below:

| Compound of Example No. | Application rate mg m$^{-2}$ compound (+pb) | % knockdown 10 mins | % knockdown 60 mins | % mortality 1 day | % mortality 6 days |
|---|---|---|---|---|---|
| Example 3 | 700(+700) 13 | 20 | 20 | | 20 |
| Example 9 | 700(+700) 7 | 7 | 33 | | 40 |

EXAMPLE C

The activity of compounds of the invention against grain pests was demonstrated by the exposure of *Sitophilus granarius* to deposits of the compound under test and a synergist (piperonyl butoxide) in a 1:5 ratio on grain. Mortality was assessed after 6 days.

The results are shown below:

| Compound of Example No: | Application rate ppm compound(+pb) | % mortality |
|---|---|---|
| Example 3 | 200(+1000) | 100 |
| Example 9 | 200(+1000) | 100 |

EXAMPLE D

The activity of compounds of the invention against mosquito larvae was demonstrated by the exposure of third instar larvae of *Aedes aegypti* to an aqueous suspension of the compound under test and synergist (piperonyl butoxide) in a 1:5 ratio. Mortality was assessed after 18 hours.

The results are shown below:

| Compound of Example No: | Application rate ppm compound(+pb) | % mortality |
|---|---|---|
| Example 3 | 2.5(+12.5) | 100 |
| Example 9 | 2.5(+12.5) | 100 |

EXAMPLE E

The activity of a compound of the invention against adult mosquitoes was demonstrated by application to female *Aedes aegypti* of a solution of the compound under test and a synergist (piperonyl butoxide). Knockdown was assessed after 1 hour and mortality after 24 hours.

| Compound of Example No. | Amount applied μg compound(+pb) | % knockdown | % mortality |
|---|---|---|---|
| Example 9 | 2(4) | 70 | 80 |

EXAMPLE F

Activity against the cattle tick, *Boophilus microplus*

(i) Injection

The compound was supplied as a 50 mg/litre solution in DMSO:Acetone (1:1). Administration of the compound was by means of a microapplicator which was preset to deliver 0.2 μl of solution. The compound in solution was injected into fully engorged female *Boophilus microplus*, susceptible strain, at a site just lateral to the mouthparts at the rate of 10 μg/tick. Reducing the concentration reduced the dose delivered.

After injection the ticks were maintained at 24° C. and 85% RH for 14 days. At this time the ticks were examined for the presence of viable eggs which gave the per cent inhibition of reproduction (% IR). The number of dead ticks was also noted.

The results are shown below

| Compound | Dose (μg) | No: injected | No.laying viable eggs | No. dead | % IR | % Kill |
|---|---|---|---|---|---|---|
| Example 9 | 10 | 10 | 1 | 3 | 90 | 30 |
| | 5 | 10 | 3 | 1 | 70 | 10 |
| | 1 | 10 | 8 | 0 | 20 | 0 |

(ii) Immersion

The compound was supplied as a 100 mg/liter solution in Esso 200/wetters. Dilution with water gave the required concentrations.

(iii)Adults

Groups of 20 fully engorged female *B.microplus* susceptible strain were placed in a mesh basket which was immersed in the test dilution for 10 minutes. After immersion the ticks were removed, dried and then fixed to double-sided adhesive tape which was itself affixed to white plastic boards. The boards holding the ticks were held at 24° C. and 85% RH for 14 days.

Individual egg masses were scored from 0-4 for quality and quantity and the total score for each group was obtained. The scores were corrected for water control oviposition, plotted on log-probit paper and the % concentration inhibiting 50% and 99% of viable oviposition determined.

The results are shown below:

| | B.microplus (susceptible) | | | |
|---|---|---|---|---|
| Compound | IR50 (%) | IR99 (%) | LC50 (%) | LC99 (%) |
| Example 9 | 0.026 | 0.1 | 0.1 | 0.1 |

Larvae

Larval ticks were immersed using a published method (Shaw, R. D., Cook, M. and Carson, R. E. (1968). *J.Econ. Ent.* 61, 1590). Mortality data are presented for *B.microplus* susceptible and pyrethroid resistant strain (Malchi).

| | B.microplus Susceptible | | Malchi | |
|---|---|---|---|---|
| Compound | LC50 (%) | LC99 (%) | LC50 (%) | LC99 (%) |
| Example 9 | 0.00044 | 0.0013 | 0.00022 | 0.00065 |

EXAMPLE G

Synergism of compounds of Formula I (i) Potentiation by other unsaturated amides Female houseflies (*Musca domestica*) were treated with solutions of compounds of Formula I and a potential synergist both dissolved in butanone, the flies having been treated one hour earlier with 6 μg piperonyl butoxide (PB).

The dose required to prevent flight of half the flies 10 minutes after application of the compound (KD50) was determined and the factor of potentiation (FOP) was calculated by the Equation of the Harmonic Mean for mixtures of the compounds.

| Compound | KD50(μg/fly) | F.O.P |
|---|---|---|
| (a) N-isobutyl-(2E,4E)-decadienamide | 77 | — |
| (b) Compound of Example 9 | 8.4 | — |
| (c) Compound of Example 10 | 5.6 | — |
| (a):(b) 3:1 | <10.0 | >2.5 |
| (a):(c) 20:1 | 13.65 | 3.5 |
| (a):(c) 40:1 | 14.35 | 4.1 |

As the FOP in each case is greater than 1.0, potentiation is demonstrated.

(ii) Potentiation by pyrethroids

Solutions of the compounds were sprayed into a chamber and houseflies released into the chamber. The respective concentrations of compound (%) necessary for prevention of flight of half the flies after 4 minutes (KC50) and for death of half the flies (LC50) were determined, and the FOP calculated as above.

| Compound | KC50 | | LC50 |
|---|---|---|---|
| (a)Example 9 | 3.5 | | 1.8 |
| (b)S-bioallethrin | 0.058 | | 0.05 |
| (a):(b) 50:1 | 0.48 | (45:1) | 0.527 |

| Compound | KC50 | LC50 |
|---|---|---|
| FOP | 3.37 | 1.94 |

Potentiation is therefore demonstrated. The procedure was repeated, with minor changes in technique (hence giving differing KC50 values from those quoted above), for permethrin and deltamethrin.

| Compound | KC50 | FOP |
|---|---|---|
| (a)Example 9 | 0.22 | — |
| (b)Permethrin | 0.47 | — |
| (c)Deltamethrin | 0.035 | — |
| (a):(b)1:1 | 0.178 | 1.68 |
| (a):(c)16.75:1 | 0.071 | 2.39 |

EXAMPLE H

Interference with gamma-aminobutyric acid (GABA) release from insect synaptosomes is thought to be important in the insecticidal action of the compounds of the invention. Using published procedures (E. G. Gray and V. P. Whittaker, Journal of Anatomy 96, 79–87 (1962); G. Levi, V. Gallo and M. Raiter, Neurochemical Research 5(3), 281–295 (1980)), compounds of Formula I were compared with related compounds outside the scope of the invention.

Arranged in decreasing order of potency (release of $^3$H-labelled GABA), the compounds were:
1. Compound of Example 10
2. Analogous compound to that of Example 10 but having 3,4-methylenedioxy on phenyl ring instead of 2-trifluoromethyl.
3. Compound of Example 9
4. Analogous compound to that of Example 9 but having 3-trifluoromethyl substitution on phenyl ring.
5. Analogous compound to that of Example 9 but having 3,4-methylenedioxy substitution on phenyl ring.

It is to be noted that the 3,4-methylenedioxy compounds are related to certain natural compounds known to be insecticidal, for example piperine (Agric. Biol. Chem. 43(7) 1609–1611, 1979).

Formulations

| 1. | Emulsifiable Concentrate | |
|---|---|---|
| | Compound of Example 10 | 10.00 |
| | Ethylan KEO | 20.00 |
| | Xylene | 67.50 |
| | Butylated Hydroxyanisole | 2.50 |
| | | 100.00 |
| 2. | Wettable Powder | |
| | Compound of Example 10 | 25.0 |
| | Attapulgite | 69.50 |
| | Sodium isopropylbenzene sulphonate | 0.50 |
| | Sodium salt of condensed naphthalene sulphonic acid | 2.50 |
| | Butylated hydroxytoluene | 2.50 |
| | | 100.00 |
| 3. | Dust | |
| | Compound of Example 10 | 0.50 |
| | Butylated Hydroxyanisole | 0.10 |
| | Talc | 99.40 |
| | | 100.00 |
| 4. | Bait | |
| | Compound of Example 10 | 0.25 |
| | Icing Sugar | 99.65 |
| | Butylated hydroxy toluene | 0.10 |
| | | 100.00 |

-continued

| | | |
|---|---|---|
| 5. | Lacquer | |
| | Compound of Example 10 | 2.5 |
| | Resin | 5.0 |
| | Butylated Hydroxy anisole | 0.5 |
| | High aromatic white spirit | 92.0 |
| | | 100.00 |
| 6. | Aerosol | |
| | Compound of Example 10 | 0.30 |
| | Butylated Hydroxy anisole | 0.10 |
| | 1,1,1-Trichloroethane | 4.00 |
| | Odourless Kerosene | 15.60 |
| | Arcton 11/12. 50:50 mix | 80.00 |
| | | 100.00 |
| 7. | Spray | |
| | Compound of Example 10 | 0.1 |
| | Butylated Hydroxy anisole | 0.1 |
| | Xylene | 10.0 |
| | Odourless Kerosene | 89.8 |
| | | 100.00 |
| 8. | Potentiated Spray | |
| | Compound of Example 10 | 0.1 |
| | Permethrin | 0.1 |
| | Butylated Hydroxyanisole | 0.1 |
| | Xylene | 10.1 |
| | Odourless Kerosene | 89.8 |
| | | 100.0 |

We claim:

1. A method of controlling pests of the Order Acarina comprising applying to the pest an acaricidally effective amount of compound of formula (I)

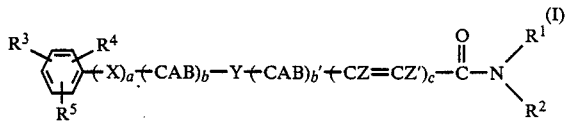

wherein:

R$^1$ and R$^2$ are the same or different and each is hydrogen, alkyl, C$_{3-8}$cycloalkyl, C$_{3-8}$cycloalkyl-alkyl, phenyl, aralkyl or alkenyl, and wherein any of the groups mentioned of R$^1$ and R$^2$ may be substituted with alkoxy, alkyl, methoxycarbonyl, halo or hydroxy, in the above definition of R$^1$ and R$^2$, alkyl, and alkenyl contain 1 to 10 carbons; R$^3$, R$^4$ and R$^5$ are each independently hydrogen, halo, alkyl, alkenyl, alkoxy having at least two carbon atoms, phenyl and wherein the groups mentioned for R$^3$, R$^4$ and R$^5$ may substituted with alkoxy, alkyl, halo or hydroxy, in the above definition of R$^3$, R$^4$ and R$^5$; alkyl, alkenyl and alkoxy contain 1 to 6 carbons;

a is 1 or 2;

each X is C≡C or CZ=CZ';

each Z and Z$^2$; is hydrogen, halo or alkyl;

Y is CAB, CH$_2$OCH$_2$ or CH$_2$S(O)$_d$CH$_2$ where d is 0, 1 or 2;

each A and B is hydrogen, alkyl or halo provided that neither A nor B is halo in a group CAB which is α to an unsaturated carbon atom;

b and b', which may be the same or different, are O or an integer from 1 to 5, b and b' together totalling not more than 7;

c is 1 or 2; and the configuration of any olefinic group conjugated to the CO group in Formula (I) is E.

2. The method of controlling pests of the Order Acarina which comprises applying to said pests of the Order Acarina an acaricidally effective amount of the compound N-isobutyl-11-(3'-trifluoromethylphenyl)-(2E,4E,8Z,10E)-undecatetrenamide or an acid addition salt thereof.

3. The method of controlling pests of the Order Acarina which comprises applying to said pests of the Order Acarina or the environment thereof an acaricidally effective amount of the compound N-isobutyl-11-(3'trifluoromethylphenyl)-(2E,4E,8Z,10E)-undecatetrenamide.

* * * * *